(12) United States Patent
Okumura et al.

(10) Patent No.: US 8,222,016 B2
(45) Date of Patent: Jul. 17, 2012

(54) RECOMBINANT C-TERMINAL α-AMIDATING ENZYME DERIVATIVE

(75) Inventors: Takeshi Okumura, Sano (JP); Kazuaki Furukawa, Tatebayashi (JP); Masayuki Yabuta, Tatebayashi (JP)

(73) Assignee: Daiichi Sankyo Company, Limited, Chuo-ku, Tokyo (JP)

(*) Notice: Subject to any disclaimer, the term of this patent is extended or adjusted under 35 U.S.C. 154(b) by 0 days.

(21) Appl. No.: 12/666,032

(22) PCT Filed: Jun. 27, 2008

(86) PCT No.: PCT/JP2008/062123
§ 371 (c)(1),
(2), (4) Date: Dec. 22, 2009

(87) PCT Pub. No.: WO2009/005140
PCT Pub. Date: Jan. 8, 2009

(65) Prior Publication Data
US 2010/0261249 A1    Oct. 14, 2010

(30) Foreign Application Priority Data

Jun. 29, 2007   (JP) ................................. 2007-173461

(51) Int. Cl.
*C12N 9/02* (2006.01)
(52) U.S. Cl. ........................ 435/189; 435/7.1; 530/350
(58) Field of Classification Search ............................ None
See application file for complete search history.

(56) References Cited

U.S. PATENT DOCUMENTS

| | | | | |
|---|---|---|---|---|
| 4,708,934 A | * | 11/1987 | Gilligan et al. | 435/68.1 |
| 5,871,995 A | * | 2/1999 | Iida et al. | 435/212 |

FOREIGN PATENT DOCUMENTS

| | | |
|---|---|---|
| EP | 2581527 | 11/1996 |
| EP | 2598050 | 1/1997 |
| EP | 0299790 | 1/2001 |
| JP | 02-000484 | 1/1990 |
| JP | 7-163340 | 6/1995 |
| JP | 7-250691 | 10/1995 |
| JP | 11-504819 | 5/1999 |
| JP | 2004-525630 | 8/2004 |
| WO | 96/40918 | 12/1996 |
| WO | 02/72605 | 9/2002 |

OTHER PUBLICATIONS

Seffernick et al. (J. Bacteriology, vol. 183, pp. 2405-2410, 2001).*
Hauser et al. (Biochem. Biophys. Res. Comm, vol. 241, pp. 509-512, 1997).*
Wells, Biochemistry, vol. 29, pp. 8509-8517, 1990.*
Eipper et al., "Identification in Pituitary Tissue of a Peptide α-Amidation Activity that Acts on Glycine-Extended Peptides and Required Molecular Oxygen, Copper, and Ascorbic Acid," Proc. Natl. Acad. Sci. USA, vol. 80, pp. 5144-5148, Aug. 1983, Neurobiology.
Ray et al., "Production of Recombinant Salmon Calcitonin by In Vitro Amidation of an *Escherichia coli* Produced Precursor Peptide," Bio/Technology, vol. 11, Jan. 1993, pp. 64-70.
Supplementary European Search Report mailed May 31, 2011 issued in EP Application No. 08777861.9.
Kolhekar et al., Essential Features of the Catalytic Core of Peptidyl-α-hydroxyglicine α-Amidating Lyase, Biochemistry, 2002, 41, pp. 12384-12394.
International Search Report issued on Oct. 7, 2008 in International PCT Application No. PCT/JP2008/062123 filed Jun. 27, 2008.
Williamson, M., "Definition: Peptidylglycine alpha-amitdating monooxygenase", Database DDBJ/EMBL/GenBank [online], Accession No. Q9GQN1, www.ncbi.nlm.nih.gov/entrez/viewer.fcgi?db=protein& id=74824125>28-Nov.-2006.

* cited by examiner

*Primary Examiner* — Hope Robinson
(74) *Attorney, Agent, or Firm* — Drinker Biddle & Reath LLP

(57) ABSTRACT

Disclosed are: a recombinant C-terminal α-amidated enzyme derivative which lacks the formation of at least one disulfide bond among five disulfide bonds occurring in a C-terminal α-amidated enzyme derived from *Xenopus laevis*; DNA encoding the derivative; an expression vector carrying the DNA; a bacterium *Escherichia coli* transformed with the expression vector; and a method for producing the derivative by using the bacterium *Escherichia coli*.

3 Claims, 7 Drawing Sheets

Fig. 1

UPPER LINE: Xenopus Leavis AE-I
LOWER LINE: Rat AE (PHM domein)

```
-41                                                            9
                                       1
MASLSSSFLVLFLL----FQNSCYCFRSPLSVFKRYEESTRSLSND C LGT
MAGRARSGLLLLLLGLLALQSSCLAFRSPLSVFKRFKETTRSFSNE C LGT
                                                              59
TRPVMSPGSSDYTLDIRMPGVTPTESDTYL C KSYRLPVDDEAYVVDFRPH
IGPVTPLDASDFALDIRMPGVTPKESDTYF C MSMRLPVDEEAFVIDFKPR
                                                             109
ANMDTAHHMLLFG C NIPSSTDDYWD C SAGT C MDKSSIMYAWAKNAPPTKL
ASMDTVHHMLLFG C NMPSSTGSYWF C DEGT C TDKANILYAWARNAPPTRL
                                                             159
PEGVGFRVGGKSGSRYFVLQVHYGNVKAFQDKHKD C TGVTVRVTPEKQPQ
PKGVGFRVGGETGSKYFVLQVHYGDISAFRDNHKD C SGVSVHLTRVPQPL
                                                             209
IAGIYLSMSVDTVIPPGEEAVNSDIA C LYNRPTIHPFAYRVHTHQLGQVV
IAGMYLMMSVDTVIPPGEKVVNADIS C QYKMYPMHVFAYRVHTHHLGKVV
                                                             259
SGFRVRHGKWSLIGRQSPQLPQAFYPVEHPVEISPGDIIATR C LFTGKGR
SGYRVRNGQWTLIGRQNPQLPQAFYPVEHPVDVTFGDILAAR C VFTGEGR
                                                             309
TSATYIGGTSNDEM C NLYIMYYMDAAHATSYMT C VQTGEPKLFQNIPEIA
TEATHIGGTSSDEM C NLYIMYYMEAKYALSFMT C TKNVAPDMFRTIPAEA
                                                             359
NVPIPVSPDMMMMMGHGHHHTEAE-PEKNTGLQQPKREEEEVLDQGLITL
NIPIPVKPDMVMMHGH---HKEAENKEKSALMQQPKQGEEEVLEQGDFYS

GDSAV

LLS--
```

| | | |
|---|---|---|
| P1' | AEp003 SEQ ID NO 3: | 5'-ATT GGATCC GGGAACCACGCGGCC |
| P4 | AEp004 SEQ ID NO 4: | 5'-TCACCCCCGTGGCATCTTTATGT |
| P5 | AEp005 SEQ ID NO 5: | 5'-ACATAAAGATGCCACGGGGGTGA |
| P6 | AEp006 SEQ ID NO 6: | 5'-TGC CTCGAG TTACATCATCATGTCAGGGCT |

AE-I [1-321] (C40A/C85A)

| | | |
|---|---|---|
| P1 | AEp007 SEQ ID NO 7: | 5'-ATT GGATCC GTCACTTTCCAATGACTGCTT |
| P2 | AEp008 SEQ ID NO 8: | 5'-GGTAAGACTTGGCCAAATATGTG |
| P3 | AEp009 SEQ ID NO 9: | 5'-CACATATTTGGCCAAGTCTTACC |
| P4 | AEp010 SEQ ID NO 10: | 5'-TTCCCGCACTAGCGTCCCAGTAA |
| P5 | AEp011 SEQ ID NO 11: | 5'-TTACTGGGACGCTAGTGCGGGAA |
| P6 | AEp006 SEQ ID NO 6: | 5'-TGC CTCGAG TTACATCATCATGTCAGGGCT |

AE-I [1-321] (C73A/C90A)

| | | |
|---|---|---|
| P1 | AEp007 SEQ ID NO 7: | 5'-ATT GGATCC GTCACTTTCCAATGACTGCTT |
| P2 | AEp012 SEQ ID NO 12: | 5'-AAGGTATATTGGCTCCAAATAGA |
| P3 | AEp013 SEQ ID NO 13: | 5'-TCTATTTGGAGCCAATATACCTT |
| P4 | AEp014 SEQ ID NO 14: | 5'-ATTTGTCCATGGCAGTTCCCGCA |
| P5 | AEp015 SEQ ID NO 15: | 5'-TGCGGGAACTGCCATGGACAAAT |
| P6 | AEp006 SEQ ID NO 6: | 5'-TGC CTCGAG TTACATCATCATGTCAGGGCT |

AE-I [1-321] (C186A/C293A)

| | | |
|---|---|---|
| P1 | AEp007 SEQ ID NO 7: | 5'-ATT GGATCC GTCACTTTCCAATGACTGCTT |
| P2 | AEp016 SEQ ID NO 16: | 5'-TGTTGTAGAGGGCGGCGATATCA |
| P3 | AEp017 SEQ ID NO 17: | 5'-TGATATCGCCGCCCTCTACAACA |
| P4 | AEp018 SEQ ID NO 18: | 5'-CCGTCTGTACAGCGGTCATGTAT |
| P5 | AEp019 SEQ ID NO 19: | 5'-ATACATGACCGCTGTACAGACGG |
| P6 | AEp006 SEQ ID NO 6: | 5'-TGC CTCGAG TTACATCATCATGTCAGGGCT |

AE-I [1-321] (C252A/C274A)

| | | |
|---|---|---|
| P1 | AEp007 SEQ ID NO 7: | 5'-ATT GGATCC GTCACTTTCCAATGACTGCTT |
| P2 | AEp020 SEQ ID NO 20: | 5'-CAGTGAACAGAGCCCTGGTTGCT |
| P3 | AEp021 SEQ ID NO 21: | 5'-AGCAACCAGGGCTCTGTTCACTG |
| P4 | AEp022 SEQ ID NO 22: | 5'-TGTATAAATTAGCCATTTCATCG |
| P5 | AEp023 SEQ ID NO 23: | 5'-CGATGAAATGGCTAATTTATACA |
| P6 | AEp006 SEQ ID NO 6: | 5'-TGC CTCGAG TTACATCATCATGTCAGGGCT |

| | | |
|---|---|---|
| P1' AEp003 SEQ ID NO 3: | 5' | -ATT`GGATCC`LGGGAACCACGCGGCC |
| P2 AEp008 SEQ ID NO 8: | 5' | -GGTAAGACTT<u>GGC</u>CAAATATGTG |
| P3 AEp009 SEQ ID NO 9: | 5' | -CACATATTT<u>GGC</u>CAAGTCTTACC |
| P4 AEp010 SEQ ID NO 10: | 5' | -TTCCGCACT<u>AGC</u>GTCCCAGTAA |
| P5 AEp011 SEQ ID NO 11: | 5' | -TTACTGGGAC<u>GCT</u>AGTGCGGGAA |
| P6 AEp006 SEQ ID NO 6: | 5' | -TGC`CTCGAG`TTACATCATCATGTCAGGGCT |

AE-I [1-321] (C40A/C85A/C252A/C274A)

| | | |
|---|---|---|
| P1 AEp007 SEQ ID NO 7: | 5' | -ATT`GGATCC`ATCACITTCCAATGACTGOTT |
| P2 AEp020 SEQ ID NO 20: | 5' | -CAGTGAACAG<u>AGC</u>CCTGGTTGCT |
| P3 AEp021 SEQ ID NO 21: | 5' | -AGCAACCAGG<u>GCT</u>CTGTTCACTG |
| P4 AEp022 SEQ ID NO 22: | 5' | -TGTATAAATT<u>AGC</u>CATTTCATCG |
| P5 AEp023 SEQ ID NO 23: | 5' | -CGATGAAATG<u>GCT</u>AATTTATACA |
| P6 AEp006 SEQ ID NO 6: | 5' | -TGC`CTCGAG`TTACATCATCATGTCAGGGCT |

Fig.7

PROTEIN CONCENTRATION
AFTER DIALYSIS (mg/L)

| AMIDATING ENZYME AND ITS DERIVATIVES | | ENZYME ACTIVITY (U/mL) | ACTIVITY/PROTEIN CONCENTRATION (U/mg) | ACTIVITY/1mL OF MEDIUM (U/mL) | COMPARED WITH AE-1 [1-321] |
|---|---|---|---|---|---|
| AE-1 [1-321] | 200 | 41.1 | 205.4 | 26.7 | 100.0% |
| AE-1 [8-321] (C145A) | 281 | 236.1 | 840.3 | 109.2 | 409.1% |
| AE-1 [1-321] (C40A/C85A) | 249 | 447.7 | 1797.9 | 233.7 | 875.3% |
| AE-1 [1-321] (C73A/C90A) | 287 | 16.1 | 56.1 | 7.3 | 27.3% |
| AE-1 [1-321] (C186A/C293A) | 213 | - | - | - | - |
| AE-1 [1-321] (C252A/C274A) | 452 | 122.4 | 270.7 | 35.2 | 131.8% |
| AE-1 [8-321] (C145A,C40A/C85A) | 273 | 212.4 | 778.1 | 101.1 | 378.8% |
| AE-1 [1-321] (C40A/C85A,C252A/C274A) | 245 | 553.6 | 2259.6 | 293.7 | 1100.1% |

RECOMBINANT C-TERMINAL α-AMIDATING ENZYME DERIVATIVE

CROSS REFERENCE TO RELATED APPLICATIONS

This application is the National Stage of International Application No. PCT/JP2008/062123 filed Jun. 27, 2008, and claims benefit of Japanese Patent Application No. 2007-173461 filed Jun. 29, 2007, which are herein incorporated by reference in their entirety.

REFERENCE TO A SEQUENCE LISTING

A Sequence Listing containing SEQ ID NOS: 1-37 is incorporated herein by reference.

FIELD OF THE INVENTION

The present invention relates to a recombinant C-terminal α-amidating enzyme derivative in which at least one of the five disulfide bonds to be normally owned by C-terminal α-amidating enzyme derived from *Xenopus laevis* has not been formed, DNA encoding said derivative, an expression vector containing said DNA, an *Escherichia coli* (*E. coli*) transformed with said expression vector, and a method of producing said derivative using said *E. coli*.

Specifically the present invention relates to a recombinant C-terminal α-amidating enzyme derivative of which enzyme activity has been enhanced by inhibiting the formation of at least one specific disulfide bond of the five disulfide bonds capable of being formed during refolding in the production of C-terminal α-amidating enzyme using a gene recombinant technology.

BACKGROUND ART

C-terminal α-amidating enzyme (peptidyl-glycine alpha-amidating monooxygenase I, EC 1.14.17.3) is present in eukaryotic organisms and forms the C-terminal amide structure of some biologically active peptides (peptide hormones, neuropeptides, peptide toxins etc.) or proteins. The C-terminal amide structure is known to be indispensable for the expression of biological activities of these peptides or proteins. In the case of human calcitonin, for example, it is known when the native C-terminal proline amide residue is converted to a proline residue, the biological activity decreases to as low as $1/1600$ of the original activity.

Also, the *Xenopus laevis* C-terminal α-amidating enzyme per se has been disclosed in Japanese Patent No. 2598050 (registered on Jan. 9, 1997) and its coding gene has been disclosed in Japanese Patent No. 2581527 (registered on Nov. 21, 1996), respectively.

From the structural analysis of precursors of peptides and proteins having the C-terminal amide structure, it was found that in substrates for C-terminal α-amidating enzymes there is always glycine (Gly) present at the C-terminal end of the residue to be amidated (conversion of a —COOH group to a —CONH$_2$ group), which is represented by a general formula R-X-Gly wherein X represents any amino acid residue to be α-amidated at the C-terminus, Gly represents a glycine residue, and R represents the rest of said peptide or protein. On this Gly, a two-stage reaction of oxidation via a copper ion (first stage: hydroxylation of the α-carbon of Gly) and dealkylation (second stage: release of glyoxylic acid) takes place so that the C-terminus of the substrate is amidated. It is reported that in order to obtain the maximum enzyme activity of this amidating enzyme, ascorbic acid in addition to molecular oxygen and copper ion ($Cu^{2+}$) are required (see Betty A. Eipper, Richard E. Mains, and Christopher C. Glembotski, "Identification in Pituitary Tissue of a Peptide-amidation Activity That Acts on Glycine-Extended Peptides and Requires Molecular Oxygen, Copper and Ascorbic Acid" Proc. Natl. Acad. Sci. U.S.A. 80, 5144-5148, 1983).

Generally since such modifications including amidation, phosphorylation and acylation take place after translation from mRNA, they are called post-translational modifications, phenomena that are only observed in eucaryotic cells. Prokaryotic cells such as *E. coli* that is widely used in the production of recombinant proteins and peptides are incapable of such a post-translational modification. Considering the biosynthetic mechanisms of amidated peptides by eucaryotic cells that have been elucidated to date, amidated peptides can be produced in large quantities by gene recombinant technology using prokaryotic cells such as *E. coli*.

An amidated peptide can be produced in large quantities and at low cost by a method in which an amidated peptide precursor represented by a general formula R-X-Gly is expressed in large quantities as a recombinant in prokaryotic cells such as *E. coli*, a C-terminal α-amidating enzyme derived from eucaryotic cells is secured in large quantities, and said amidated peptide precursor is treated with said C-terminal α-amidating enzyme in vitro in an optimal reaction condition for producing an amidated peptide to produce the amidated peptide. In fact, efforts to produce amidated peptides by such a method has been made up to now, as described below.

Unigene Laboratories, Inc., Fairfield, N.J. 07004, "Production of recombinant salmon calcitonin by in vitro amidation of an *Escherichia coli* produced precursor peptide." Biotechnology (NY), 1993 January; 11(1):64-70 reports a method in which a salmon calcitonin (sCT) recombinantly produced using *Escherichia coli* was fused to part of glutathione S-transferase and expressed, sulfonated, and cleaved with cyanogen bromide, and using a C-terminal α-amidating enzyme expressed separately in CHO cells, the C-terminus of sCT was amidated in vitro.

Kokai (Japanese Unexamined Patent Publication) No. 7-163340 also describes a method of producing a human-derived calcitonin (hCT) using an amidating enzyme that was similarly expressed in CHO cells.

In these methods, the C-terminal α-amidating enzymes used in amidating the C-terminus of a protein of interest were produced by the CHO cell which is an animal cell.

Generally, however, the production of a recombinant protein using an animal cell takes a long culturing time and thus poses problems such as low productivity per unit time. As a method for resolving this problem, a method of using *E. coli* that enables production in a shorter culturing time has been developed as exemplified in Kokai (Japanese Unexamined Patent Publication) No. 7-250691.

This method permits the expression of a *Xenopus laevis* C-terminal α-amidating enzyme (peptidyl-glycine alpha-amidating monooxygenase I, EC 1.14.17.3) in large quantities by a recombinant technology in *E. coli*. However, most of the C-terminal α-amidating enzyme and derivatives thereof expressed by this method are forming inclusion bodies (a mass of inactive protein having the same amino acid sequence but does not have a higher-order structure, and thus is called insoluble granules) in *E. coli* and do not exhibit the activity of the C-terminal α-amidating enzyme.

Thus, an inert enzyme produced by such a method must be converted by some means (for example, refolding) to an active form. For this purpose, in the invention described in Kokai (Japanese Unexamined Patent Publication) No. 7-250691, the C-terminal α-amidating enzyme expressed in *E. coli* was treated with a denaturing agent such as urea or guanidine hydrochloride, and then was refolded by lowering the concentration of the denaturing agent. However, the activity of the enzyme obtained by this method was about 10-15 mU per mL of the culture liquid, which was lower than that (2,860 U/mL culture liquid) of the amidating enzyme expressed in CHO cells described in the invention of Kokai (Japanese Unexamined Patent Publication) No. 7-163340.

DISCLOSURE OF THE INVENTION

Thus, it is an object of the present invention to provide a recombinant C-terminal α-amidating enzyme derivative that has a high enzyme activity compared to a conventional enzyme obtained by a gene recombinant technology using *E. coli*.

The present invention provides a recombinant C-terminal α-amidating enzyme derivative that has a high enzyme activity compared to a conventional enzyme obtained by a gene recombinant technology using *E. coli* by a method wherein a recombinant C-terminal α-amidating enzyme derivative of which amino acid sequence has been altered so as to prevent the formation of at least one specific disulfide bond of the five disulfide bonds that can be formed during refolding in the production, using a gene recombinant technology, of a *Xenopus laevis* C-terminal α-amidating enzyme derived having the amino acid sequence set forth in SEQ ID NO: 2 is expressed in *E. coli*, and the inclusion body obtained is solubilized under a non-reducing condition and subjected to a refolding procedure.

Specifically the above problem may be resolved by the following [1] to [7]:

[1] A recombinant C-terminal α-amidating enzyme derivative comprising:

(a) a polypeptide having an amino acid sequence in which at least one cysteine residue selected from the group consisting of cysteine residues at positions 6, 145, 40, 85, 252, and 274 has been altered in the amino acid sequence set forth in SEQ ID NO: 2; or (b) a polypeptide having an amino acid sequence in which one or a few amino acid residues out of the amino acid residues other than the cysteine residue have been deleted, substituted, or added in the altered amino acid sequence described in the above (a) and having the activity of C-terminal α-amidating enzyme;

wherein at least one disulfide bond has not been formed out of the bonds between the cysteine residues at positions 6 and 145, between the cysteine residues at positions 40 and 85, and between the cysteine residues at positions 252 and 274.

[2] The C-terminal α-amidating enzyme derivative according to the above [1] wherein a disulfide bond has been formed between the cysteine residues at positions 73 and 90 and between the cysteine residues at positions 186 and 293 in the amino acid sequence set forth in SEQ ID NO: 2.

[3] The C-terminal α-amidating enzyme derivative according to the above [1] or [2] wherein said alteration is substitution with another amino acid or deletion of an amino acid.

[4] The C-terminal α-amidating enzyme derivative according to the above [1] to [3] that is AE-I [1-321] (C40A/C85A) (SEQ ID NO: 27), AE-I [1-321] (C252A/C274A) (SEQ ID NO: 33), AE-I [1-321] (C40A/C85A, C252A/C274A) (SEQ ID NO: 37), AE-I [8-321] (C145A) (SEQ ID NO: 25), or AE-I [8-321] (C145A, C40A/C85A) (SEQ ID NO: 35).

[5] DNA encoding the recombinant C-terminal α-amidating enzyme derivative according to any one of the above [1] to [4].

[6] An expression vector containing the DNA according to the above [5].

[7] An *Escherichia coli* transformed with the expression vector according to the above [6].

[8] A method of producing the recombinant C-terminal α-amidating enzyme derivative according to any one of the above [1] to [4], said method comprising the steps of culturing the *Escherichia coli* according to the above [7], allowing the recombinant C-terminal α-amidating enzyme derivative to be expressed, and then recovering the derivative thus obtained.

BRIEF EXPLANATION OF THE DRAWINGS

FIG. 1 shows a comparison of the amino acid sequence of the *Xenopus laevis* C-terminal α-amidating enzyme (SEQ ID NO: 39) and that of a rat C-terminal α-amidating enzyme (SEQ ID NO: 40). The upper row represents the amino acid sequence of the *Xenopus laevis* enzyme and the lower row represents that of the rat enzyme. The sequences shown here have a signal sequence at the N-terminal end and a transmembrane domain at the C-terminal end of the mature protein of the C-terminal α-amidating enzyme. The underlined parts show the amino acid residues conserved in both species, indicating a homology of about 65%. The boxed parts indicate the cysteine residues of both species, indicating that they are highly conserved.

FIG. 4 shows the base sequences of DNA primers for obtaining the gene fragments of the derivatives AE-I [8-321] (C145A) (SEQ ID NO: 25), AE-I [1-321] (C40A/C85A) (SEQ ID NO: 27), AE-I [1-321] (C73A/C90A) (SEQ ID NO: 29), AE-I [1-321] (C186A/C293A) (SEQ ID NO: 31), and AE-I [1-321] (C252A/C274A) (SEQ ID NO: 33). The boxed parts show the restriction enzymes BamHI (GGATCC) and XhoI (CTCGAG). The one base-insertion site of guanine (G) for adjusting the reading frame and the termination codon are underlined. The mutation site where cysteine is substituted with alanine is double underlined.

FIG. 5 shows the base sequences of DNA primers for obtaining the gene fragments of the derivatives AE-I [8-321] (C145A, C40A/C85A) (SEQ ID NO: 35), and AE-I [1-321] (C40A/C85A, C252A/C274A) (SEQ ID NO: 37). The boxed parts show the restriction enzymes BamHI (GGATCC) and XhoI (CTCGAG). The one base-insertion site of guanine (G) for adjusting the reading frame and the termination codon are underlined. The mutation site where cysteine is substituted with alanine is double underlined.

Figure 2:
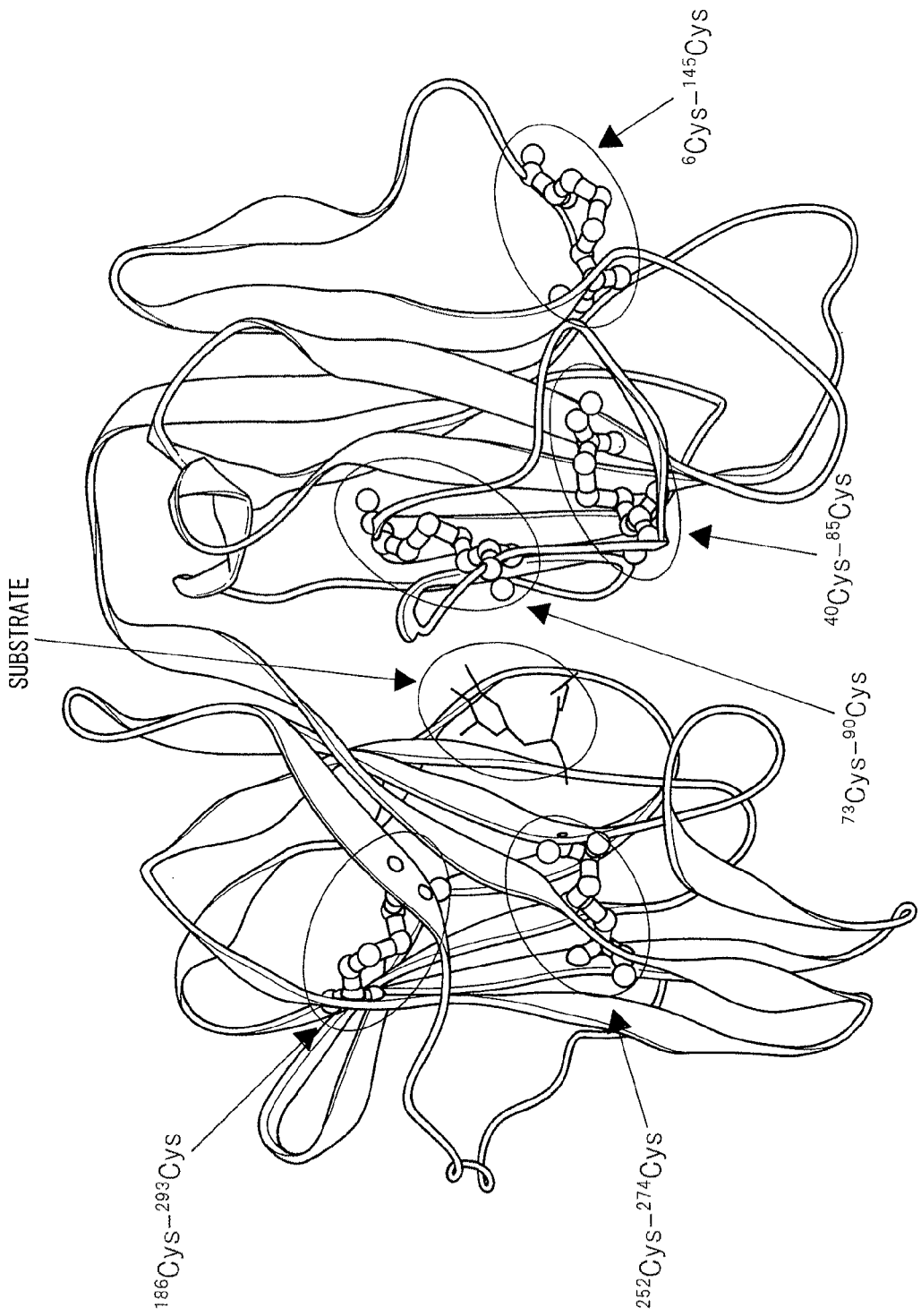
FIG. 2 is a drawing that shows the putative sites of S—S bond in the C-terminal α-amidating enzyme derived from *Xenopus laevis*. As can be seen from FIG. 2, it may be estimated that five pairs of S—S bonds are formed between $^{6}$Cys-$^{145}$Cys, $^{40}$Cys-$^{85}$Cys, $^{73}$Cys-$^{90}$Cys, $^{186}$Cys-$^{293}$Cys, and $^{252}$Cys-$^{274}$Cys

Lanes 1 and 13: Marker (molecular weight: 175, 83, 62, 47.5, 32.5, 25, 16.5, 6.5 kDa)
Lane 2: AE-I [1-321] (SEQ ID NO: 2)
Lane 3: AE-I [8-321] (C145A) (SEQ ID NO: 25)
Lane 4: AE-I [1-321] (C40A/C85A) (SEQ ID NO: 27)
Lane 5: AE-I [1-321] (C73A/C90A) (SEQ ID NO: 29)
Lane 6: AE-I [1-321] (C186A/C293A) (SEQ ID NO: 31)

Lane 7: AE-I [1-321] (C252A/C274A) (SEQ ID NO: 33)
Lane 8: AE-I [8-321] (C145A, C40A/C85A) (SEQ ID NO: 35)
Lane 11: AE-I [1-321] (C40A/C85A, C252A/C274A) (SEQ ID NO: 37)
Lanes 9, 10, and 12: -.

FIG. 7 represents a table showing the result of measuring the protein concentration and enzyme activity of the amidating enzymes and derivatives thereof after dialysis. FIG. 7 discloses the amidating enzyme constructs as SEQ ID NOS 2, 25, 27, 29, 31, 33, 35 and 37, respectively, in order of appearance.

BEST MODE FOR CARRYING OUT THE INVENTION

As described above, with regard to a problem that the C-terminal α-amidating enzyme expressed in *E. coli* is expressed as an inclusion body having no activity, the invention described in Kokai (Japanese Unexamined Patent Publication) No. 7-250691 partially resolved this problem by treating the inclusion body expressed in *E. coli* with a denaturing agent such as urea or guanidine hydrochloride and then by refolding it. However, the enzyme activity of the enzyme obtained by this method was as low as about 10-15 mU per mL of the culture liquid.

The present inventors assumed that the reason for such a low enzyme activity is that the plurality of cysteine residues present in the *Xenopus laevis* C-terminal α-amidating enzyme (said enzyme has ten cysteine residues, i.e. five pairs of S—S bonds, in the molecule) having the amino acid sequence set forth in SEQ ID NO: 2 cannot form the same disulfide bonds (S—S bonds) as those of the native form, i.e. erroneous S—S bonding is taking place during refolding.

The positions of S—S bonds in the *Xenopus laevis* C-terminal α-amidating enzyme have not been elucidated yet. Thus the present inventors investigated the homology of the amino acid sequence of a rat C-terminal α-amidating enzyme for which the positions of S—S bonds had been identified with that of a *Xenopus laevis* C-terminal α-amidating enzyme, and demonstrated that they have a high homology of 65.2% and the positions of cysteine residues in the regions corresponding to the amino acid sequence set forth in SEQ ID NO: 2 are completely conserved. And thus the present inventors assumed that the positions of S—S bonds are identical in them.

Thus, in order to prove the assumption that erroneous S—S bonding is taking place during refolding, the present inventors planned to use a *Xenopus laevis* C-terminal α-amidating enzyme and substitute a specific cysteine included in its amino acid sequence with alanine or delete it so as to create a recombinant C-terminal α-amidating enzyme derivative that were modified so that at least one pair of the five pairs of disulfide bonds capable of being formed by said enzyme derivative cannot be formed, and to obtain a recombinant C-terminal α-amidating enzyme derivative having a higher enzyme activity at a high yield by reducing the likelihood of erroneous S—S bonding to a minimum.

In the field of the present invention, with reference to a protein having a S—S bond in the molecule, it is common to newly introduce a S—S bond and to stabilize said protein in order to obtain said protein having a higher enzyme activity, as described in many reports such as Shimizu-Ibuka A. et al., "Effect of disulfide-bond introduction on the activity and stability of the extended-spectrum class A beta-lactamase Toho-1." Biochim. Biophys. Acta. 2006 August; 1764(3):1349-55, Epub 2006 Jun. 27, and Siadat O R et al., "The effect of engineered disulfide bonds on the stability of *Drosophila melanogaster* acetylcholinesterase." BMC Biochem. 2006 Apr. 16; 7:12. In Siadat O R et al., by newly introducing a S—S bond to acetylcholinesterase, the stability of the enzyme at 50° C. was successfully raised by about 170-fold compared to the wild type and resistance to denaturing agents, organic solvents, and proteases was successfully conferred.

In contrast, there are no reports to date on a method of achieving enhanced enzyme activity and stability by removing a S—S bond from a protein of interest as described in the present invention. In other words, those skilled in the art had presumed that since the removal of a S—S bond is likely to induce the reduction in the structural stability and activity of a protein of interest, it should be difficult to obtain the protein of interest having the desired activity by removing a S—S bond.

DEFINITION OF TERMS

As used herein the numbers in the amino acid sequence set forth in SEQ ID NO: 2 have been conferred with the serine residue at the N-terminal of the mature protein of C-terminal α-amidating enzyme (peptidyl-glycine alpha-amidating monooxygenase I, EC 1.14.17.3) being set as No. 1. As used herein, the positions of cysteine residues represent amino acid No. 6, 40, 73, 85, 90, 145, 186, 252, 274, and 293, respectively, in SEQ ID NO: 2.

As used herein the term "alteration" with reference to the cysteine residue represents, nonrestrictively, modification such as the deletion of said cysteine residue, substitution with another amino acid residue, the removal of an amino acid sequence having said cysteine residue or the addition of a protecting group to the thiol group of said cysteine residue, and encompasses any of the modifications that avoid the formation of a disulfide bond between the cysteine residues at positions 6 and 145, between the cysteine residues at positions 40 and 85, and between the cysteine residues at positions 252 and 274.

As used herein the term "C-terminal α-amidating enzyme" means an enzyme having an ability of catalyzing oxidation via copper ion (first stage: hydroxylation of a carbon of Gly) in the amidation (conversion of a —COOH group to a —CONH$_2$ group) of a glycine residue at the C-terminal end of the precursor of a peptide or protein having a C-terminal amide structure, and specifically means an enzyme having the amino acid sequence set forth in SEQ ID NO: 2.

As used herein the term "C-terminal α-amidating enzyme derivative" means an enzyme having an amino acid sequence in which the amino acid sequence of the above C-terminal α-amidating enzyme has been altered.

As used herein the term "C-terminal α-amidating enzyme activity" means an enzyme activity similar to that of the C-terminal α-amidating enzyme (peptidyl-glycine alpha-amidating monooxygenase I, EC 1.14.17.3) derived from *Xenopus laevis*.

As used herein the term "AE-I [1-321] (C40A/C85A)" means a polypeptide having an amino acid sequence (SEQ ID NO: 27) which has the primary sequence (SEQ ID NO: 2) of the amino acids in a region corresponding to from the serine residue at position 1 to the methionine residue at position 321 among the mature protein of the *Xenopus laevis* C-terminal α-amidating enzyme (peptidyl-glycine alpha-amidating monooxygenase I, EC 1.14.17.3), and in which the cysteine residue at position 40 has been substituted with an alanine residue and the cysteine residue at position 85 has been substituted with an alanine residue. The term "AE-I [1-321]", the term "AE-I [1-321] (C252A/C274A)" (SEQ ID NO: 33), the term "AE-I [1-321] (C40A/C85A, C252A/C274A)" (SEQ ID NO: 37), the term "AE-I [1-321] (C73A/C90A)" (SEQ ID NO: 29), and the term "AE-I [1-321] (C186A/C293A)" (SEQ ID NO: 31) have a similar meaning. Except for "AE-I [1-321] (SEQ ID NO: 2)," they are simply termed as derivatives of C-terminal α-amidating enzyme.

As used herein the term "AE-I [8-321] (C145A)" means a polypeptide having an amino acid sequence (SEQ ID NO: 25) in which a region from the serine residue at position 1 to the leucine residue at position 7 has been deleted, a region from the glycine residue at position 8 to the methionine residue at position 321 is present, and the cysteine residue at position 145 has been substituted with an alanine residue in the primary sequence of amino acids comprising the serine residue at position 1 to the methionine residue at position 321 excluding a signal sequence comprising 37 amino acids present at the N-terminal end. Herein, by deleting a fragment from the serine residue at position 1 to the leucine residue at position 7, the cysteine residue at position 6 has been deleted. The term "AE-I [8-321] (C145A, C40A/C85A)" means a polypeptide having an amino acid sequence (SEQ ID NO: 35) in which a region from the glycine residue at position 8 to the methionine residue at position 321 are present as described above, and the cysteine residue at position 145 has been substituted with an alanine residue, the cysteine residue at position 40 has been substituted with an alanine residue, and the cysteine residue at position 85 has been substituted with an alanine residue. This is simply termed as a derivative of C-terminal α-amidating enzyme.

Method of Measuring Enzyme Activity and Unit

When the enzyme is expressed in *E. coli*, the majority of it may be recovered in the precipitate fraction after cell disruption. Thus for the measurement of the enzyme activity, a sample prepared by solubilizing the precipitate fraction with 6M guanidine hydrochloride and then dialyzing with a guanidine hydrochloride solution is used. Generally, the enzyme activity can be determined by using a substrate represented by R-X-Gly or an amidated peptide expressed and converting it to R—X—CONH$_2$ (e.g., the conversion of a synthetic substrate [$^{125}$I]-Ac-Tyr-Phe-Gly to [$^{125}$I]-Ac-Tyr-Phe-NH$_2$). Thus, a labelled substrate (labelled R-X-Gly) is first reacted to a test enzyme solution in a Tris-HCl buffer. The Tris-HCl buffer and ethyl acetate is added thereto, and after mixing, it is separated by centrifugation to the organic solvent phase and the aqueous phase. Here, since the majority of the unreacted labelled substrate (labelled R—X-Gly) migrates to the aqueous phase and the amidated labelled substrate (labelled R—X—CONH$_2$) to the organic solvent phase, they can be easily separated. The rate of conversion to the C-terminal α-amidated product can be determined from the ratio of radioactivity of the organic solvent phase to the total radioactivity. In the present determination method, the enzyme activity in which 50% of 1 pmol of the labelled R-X-Gly (substrate) is converted to the labelled R—X—CONH$_2$ per hour is defined as one Unit.

The amidating enzyme activity was assessed by dealkylation the enzyme through the addition of an alkali (sodium hydroxide) after the oxidation reaction.

Thus, 2 μl, 10 μl, and 100 μl each of a sample to be determined was taken and added to distilled water to make a total volume of 100 μl. Then 10 mM ascorbic acid (25 μl), 200 μM copper sulfate (25 μl), 20 mg/mL catalase (1.25 μl), 1% Lubrol (20 μl), [$^{125}$I]-Ac-Tyr-Phe-Gly (2 μmol), 1M Tris-HCl (pH 7.0, 50 μl) and distilled water (25 μl) were added thereto, and reacted at 37° C. for 1 hour. After the reaction, 250 mM NaOH (250 μl) was added to the reaction mixture, mixed, and after allowing to stand at room temperature for 15 minutes (dealkylation), 1M Tris-HCl (pH 7.0, 500 μl) and ethyl acetate (2 mL) were added thereto, mixed, and centrifuged. Then, 1 mL of the ethyl acetate layer was aliquoted, and the radioactivity of it and of the rest of the solution were measured using a gamma counter to determine the ratio of radioactivity that migrated to the ethyl acetate layer. That the C-terminal amidated [$^{125}$I]-Ac-Tyr-Phe-CONH$_2$ migrates specifically to the ethyl acetate layer in this method has been confirmed by determination with a liquid chromatography or a gamma counter. The enzyme activity in which 50% of 1 pmol of the labelled R-X-Gly (substrate) is converted to the labelled R—X—CONH$_2$ per hour is defined as one Unit.

FIG. 1 shows an alignment of the amino acid sequence of the *Xenopus laevis* C-terminal α-amidating enzyme (peptidyl-glycine alpha-amidating monooxygenase I, EC 1.14.17.3) claimed in the present invention and that of a rat enzyme of which crystal structure has already been analyzed in Prigge S T, Kolhekar A S, Eipper B A, Mains R E, Amzel L M. "Amidation of biactive peptides: the structure of peptidylglycine alpha-hydroxylating monooxygenase." Science 1997 Nov. 14; 278(5341):1300-5. As can be seen from FIG. 1, they have a high homology of 65.2%, and the positions of cysteine residues present in the region corresponding to the amino acid sequence set forth in SEQ ID NO: 2 are completely conserved.

FIG. 2 shows a conformational structure of a rat C-terminal α-amidating enzyme of which crystal structure has been analyzed by Prigge S T et al. and in which the positions of S—S bonds have been identified. The present inventors assumed that, based on the positions of S—S bonds in said conformational structure, the conformational structure of the *Xenopus laevis* C-terminal α-amidating enzyme claimed in the present invention can be maintained by forming five pairs of S—S bonds between $^6$Cys-$^{145}$Cys, $^{40}$Cys-$^{85}$Cys, $^{73}$Cys-C$^{90}$Cys-$^{186}$Cys-$^{293}$Cys, and $^{252}$Cys-$^{274}$Cys.

Based on such assumed positions of S—S bonds, recombinant polypeptides in which at least one S—S bond is not formed were created. Thus, based on a plasmid, pPROEXHTa AE-I [1-321] (SEQ ID NO: 2), comprising a sequence encoding the primary sequence of amino acids from No. 1 to 321 of the amino acid sequence of the *Xenopus laevis* C-terminal α-amidating enzyme AE-I as a wild type, plasmid were created in which at least one S—S bond is not formed. These were plasmids designed so as to be expressed in *E. coli* under the control of a trc (a fusion type of lac and trp) promoter.

By site-directed mutagenesis with pPROEXHTa AE-I [1-321] (SEQ ID NO: 2) as a template, paired cysteine residues capable of forming S—S bonds were substituted with alanine residues or deleted to create plasmids pPROEXHTa AE-I [8-321] (C145A) (SEQ ID NO: 25), pPROEXHTa AE-I [1-321] (C40A/C85A) (SEQ ID NO: 27), pPROEXHTa AE-I [1-321] (C73A/C90A) (SEQ ID NO: 29), pPROEXHTa AE-I [1-321] (C186A/C293A) (SEQ ID NO: 31), and pPROEXHTa AE-I [1-321] (C252A/C274A) (SEQ ID NO: 33) having a sequence that has been mutated so that only one of the above five pairs of S—S bonds is not formed. Furthermore, based on these derivative plasmids, plasmids pPROEXHTa AE-I [8-321] (C145A, C40A/C85A) (SEQ ID NO: 35] and pPROEXHTa AE-I [1-321] (C40A/C85A, C252A/C274A) (SEQ ID NO: 37) were created having a sequence that has been mutated so that only two pairs of the above five pairs of S—S bonds are not formed. Though the number of cysteine residues to be altered is two in the above, the number of cysteine residues to be altered is not limited to it, and it is possible that only one S—S bond is not formed by altering one cysteine residue.

By transforming E. coli using these plasmids according to a standard method, recombinant E. coli cells in which the gene of interest having the above site-directed mutation has been introduced were obtained. These recombinant E. coli cells were cultured to express the desired substance as inclusion bodies in the cells. The cells were disrupted and centrifuged to recover the inclusion bodies as the precipitate fractions. After the inclusion bodies obtained were denatured with a denaturing agent, they were subjected to refolding by diluting with a denaturant-free buffer. The amidating enzymes and derivatives thereof obtained by refolding were assessed by determining the amidating enzyme activity using a synthetic substrate.

Finally, five derivatives exhibiting an enzyme activity higher than the wild type AE-I [1-321] (SEQ ID NO: 2) were obtained (i.e., derivatives AE-I [8-321] (C145A) (SEQ ID NO: 25) AE-I [1-321] (C40A/C85A) (SEQ ID NO: 27) and AE-I [1-321] (C252A/C274A) (SEQ ID NO: 33) that cannot form one pair of S—S bond, and derivatives AE-I [8-321] (C145A, C40A/C85A) (SEQ ID NO: 35) and AE-I [1-321] (C40A/C85A, C252A/C274A) (SEQ ID NO: 37) that cannot form two pairs of S—S bonds).

It is generally estimated that the removal of a S—S bond may lead to reduced stability and reduced activity of the protein. As shown in FIG. 7, however, the present inventors succeeded in obtaining a derivative exhibiting an enzyme activity higher than the wild type for a C-terminal α-amidating enzyme by removing at least one pair of the S—S bond therein.

In said derivatives that exhibit an enzyme activity higher than the wild type, a disulfide bond had been formed between the cysteine residues at positions 73 and 90 and between the cysteine residues at positions 186 and 293 in the amino acid sequence set forth in SEQ ID NO: 2.

The present invention will now be explained in more detail with reference to the following examples.

EXAMPLES

Working Example 1

Preparation of a C-Terminal α-Amidating Enzyme and its Derivative (1) Creation of E. coli Expression Plasmids pPROEXHTa AE-I [8-321] (C145A) (SEQ ID NO: 25), pPROEXHTa AE-I [1-321] (C40A/C85A) (SEQ ID NO: 27), pPROEXHTa AE-I [1-321] (C73A/C90A) (SEQ ID NO: 29), pPROEXHTa AE-I [1-321] (C186A/C293A) (SEQ ID NO: 31), and pPROEXHTa AE-I [1-321] (C252A/C274A) (SEQ ID NO: 33) of Derivatives The derivatives of the amidating enzyme were created based on a plasmid pPROEXHTa AE-I [1-321] (SEQ ID NO: 2) encoding the amino acid sequence comprising amino acids 1-321 of the amino acid sequence of the C-terminal α-amidating enzyme derived from Xenopus laevis. pPROEXHTa AE-I [1-321] (SEQ ID NO: 2) is a plasmid designed to be expressed in E. coli under the control of the trc (a fusion type of lac and trp) promoter. With this plasmid pPROEXHTa AE-I [1-321] (SEQ ID NO: 2) as a template, a derivative incapable of forming a S—S bond was created by replacing a pair of two cysteine residues each with an alanine residue by site-directed mutagenesis on a protein having an amino acid sequence comprising amino acids at positions 1 to 321 or 8 to 321. Since, for the derivative AE-I [8-321] (C145A) (SEQ ID NO: 25), cysteines at positions 6 and 145 of the amino acid sequence pair to form a S—S bond, the amino acid residues at positions 1 to 7 were removed in stead of substituting the cysteine residue at position 6 with an alanine residue, and the cysteine residue at position 145 was substituted with an alanine residue so that a S—S bond may not be formed between $^6$Cys-$^{145}$Cys.

Figure 3:
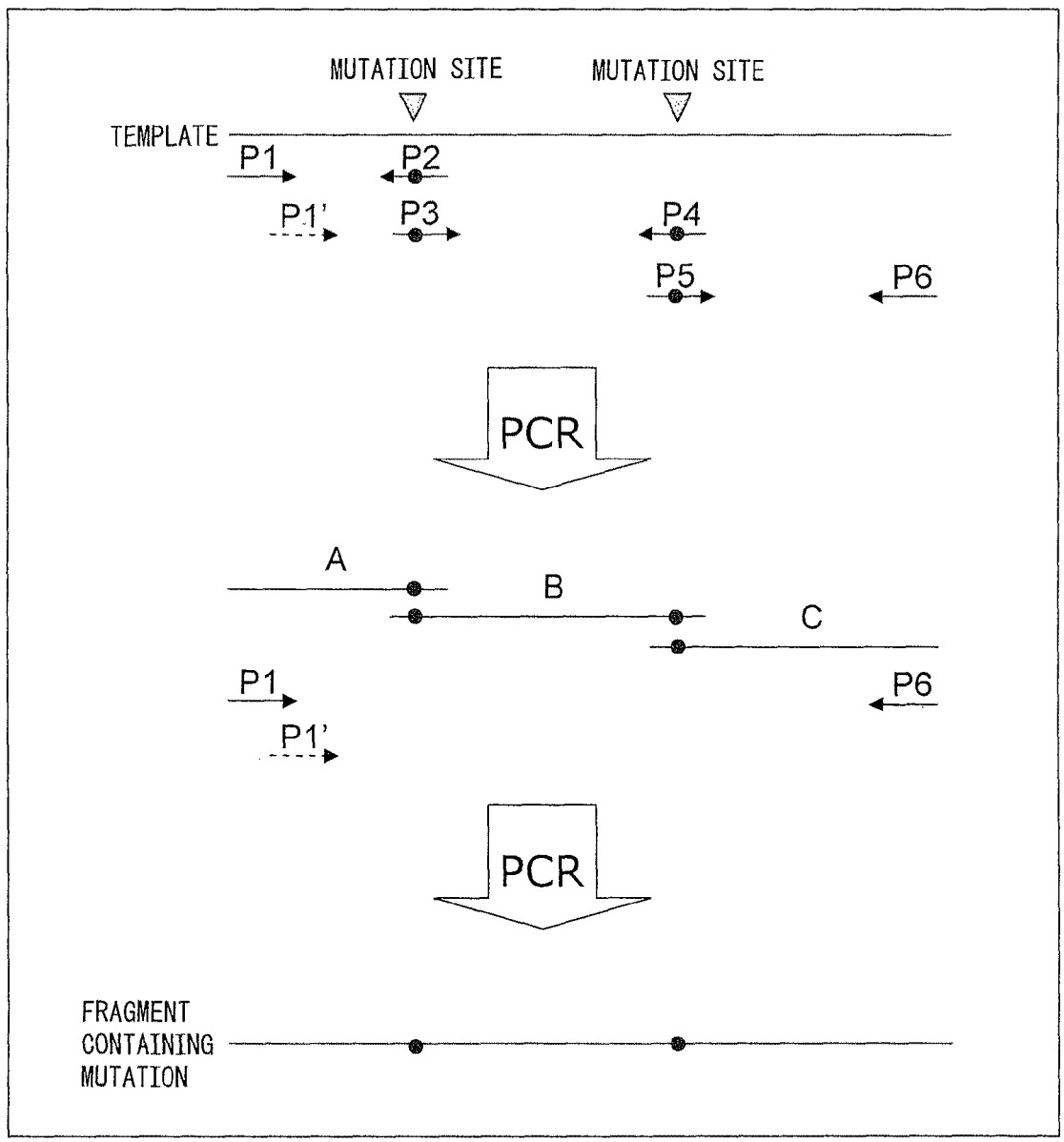
FIG. 3 is a schematic drawing of the introduction of mutation by the PCR method.

The derivative incapable of forming a pair of S—S bond was created by substituting a cysteine residue with an alanine residue by mutagenesis using a PCR method. FIG. 3 depicts an outline of the method of preparing said derivative.

First, with pPROEXHTa AE-I [1-321] (its structural gene sequence and the corresponding amino acid sequence are shown in SEQ ID NOS 1 and 2, respectively) as a template, primers for respective derivatives were created. FIG. 4 shows the sequences of primers used. In FIG. 4, primers PI and PI' have, in addition to a restriction enzyme BamHI site (boxed) at the 5'-end, guanine (underlined) inserted therein in order to adjust with the reading frame, and the primer P6 has, in addition to a restriction enzyme XhoI site (boxed) at the 5'-end, a termination codon antisense chain TTA (underlined) inserted therein. Using primers P1 and P2, P3 and P4, and P5 and P6 (or P1' and P4, and P5 and P6) (only P2, P3, P4, and P5 contain mutation) of respective derivatives, DNA fragments were amplified, and subjected to agarose gel electrophoresis and Gel Extraction Kit (Quiagen) to obtain three (or two) purified DNA fragments. Using primers P1 and P6 (or P1' and P6) (P1, P1', and P6 do not contain mutation) with the mixture of all these DNA fragments as the template, DNA fragments were PCR-amplified again to obtain an about 960 bp DNA fragment having mutation introduced therein for each derivative.

The DNA fragment obtained for each derivative was purified by the Gel Extraction Kit (Quiagen). The purified fragment was cleaved with restriction enzymes BamHI and XhoI to obtain BamHI-XhoI-digested DNA fragments, AE-I [8-321] (C145A) (SEQ ID NO: 25), AE-I [1-321] (C40A/C85A) (SEQ ID NO: 27), AE-I [1-321] (C73A/C90A) (SEQ ID NO: 29), AE-I [1-321] (C186A/C293A) (SEQ ID NO: 31), and AE-I [1-321] (C252A/C274A) (SEQ ID NO: 33). Simultaneously, after pPROEXHTa to be used as an expression vector was cleaved with restriction enzymes BamHI and XhoI, an about 4.7 kb DNA fragment containing said expression vector part was separated and purified. This product and a DNA fragment of each derivative obtained earlier were ligated with the DNA Ligation Kit (TaKaRa) to finally obtain plasmids pPROEXHTa AE-I [8-321] (C145A), pPROEXHTa AE-I [1-321] (C40A/C85A), pPROEXHTa AE-I [1-321] (C73A/C90A), pPROEXHTa AE-I [1-321] (C186A/C293A), and pPROEXHTa AE-I [1-321] (C252A/C274A) of each derivative (the structural gene sequence and the corresponding amino acid sequence of each derivative are shown in SEQ ID NO: 25, 27, 29, 31 or 33, respectively). The plasmid pPROEXHTa (Gibco) is an expression vector having the constitution of the trc (the fusion type of lac and trp) promoter, followed by His tag (His×6 tag) (SEQ ID NO: 38), a multi cloning site, and β-lactamase.

Working Example 2

Preparation of C-Terminal α-Amidating Enzyme and its Derivative (2) Creation of E. coli Expression Plasmids pPROEXHTa AE-I [8-321] (C145A, C40A/C85A) (SEQ ID NO: 35) and pPROEXHTa AE-I [1-321] (C40A/C85A, C252A/C274A) (SEQ ID NO: 37) of Derivatives Plasmids pPROEXHTa AE-I [8-321] (C145A, C40A/C85A) (SEQ ID NO: 35) and pPROEXHTa AE-I [1-321]

(C40A/C85A, C252A/C274A) (SEQ ID NO: 37) of derivatives incapable of forming two of the five pairs of S—S bonds owned by AE-I [1-321] (SEQ ID NO: 2) were created with pPROEXHTa AE-I [8-321] (C145A) (SEQ ID NO: 25) and pPROEXHTa AE-I [1-321] (C40A/C85A) (SEQ ID NO: 27) as the template. Methods of introducing mutation and creating expression vectors were similar to those in Working Example 1.

The gene fragments of the above derivatives were created using a PCR method. A method similar to the one in Working Example 1 was used. First, using primers P1 (or P1') and P2, P3 and P4, and P5 and P6 (only P2, P3, P4, and P5 contain mutation) of respective derivatives with pPROEXHTa AE-I [8-321] (C145A) (SEQ ID NO: 25) and pPROEXHTa AE-I [1-321] (C40A/C85A) (SEQ ID NO: 27) as the template, DNA fragments were amplified, and subjected to agarose gel electrophoresis and the Gel Extraction Kit (Quiagen) to obtain three purified DNA fragments. With the mixture of these three DNA fragments as the template, primers P1 (or P1') and P6 (P1, P1' and P6 do not contain mutation) were PCR-amplified again to obtain an about 960 bp DNA fragment having mutation introduced therein for each derivative. The sequences of primers are shown in FIG. 5. In FIG. 5, primers PI and PI' have, in addition to a restriction enzyme BamHI site (boxed) at the 5'-end, guanine (underlined) inserted therein in order to adjust with the reading frame, and the primer P6 has, in addition to a restriction enzyme XhoI site (boxed) at the 5'-end, a termination codon antisense chain TTA (underlined) inserted therein.

The DNA fragment obtained for each derivative was purified by the Gel Extraction Kit (Quiagen). The purified fragment was cleaved with restriction enzymes BamHI and XhoI to obtain BamHI-XhoI-digested DNA fragments, AE-I [8-321] (C145A, C40A/C85A) (SEQ ID NO: 35) and AE-I [1-321] (C40A/C85A, C252A/C274A) (SEQ ID NO: 37). Simultaneously, after pPROEXHTa to be used as an expression vector was cleaved with restriction enzymes BamHI and XhoI, an about 4.7 kb DNA fragment containing said expression vector part was separated and purified. This product and a DNA fragment of each derivative obtained earlier were ligated with the DNA Ligation Kit (TaKaRa) to finally obtain plasmids pPROEXHTa AE-I [8-321] (C145A, C40A/C85A) and pPROEXHTa AE-I [1-321] (C40A/C85A, C252A/C274A) of each derivative (the structural gene sequence and the amino acid sequence of each derivative are shown in SEQ ID NO: 35 or 37, respectively).

Working Example 3

Introduction of pPROEXHTa AE-I [1-321] (SEQ ID NO: 2), pPROEXHTa AE-I [8-321] (C145A) (SEQ ID NO: 25), pPROEXHTa AE-I [1-321] (C40A/C85A) (SEQ ID NO: 27), pPROEXHTa AE-I [1-321] (C73A/C90A) (SEQ ID NO: 29), pPROEXHTa AE-I [1-321] (C186A/C293A) (SEQ ID NO: 31), pPROEXHTa AE-I [1-321] (C252A/C274A) (SEQ ID NO: 33), pPROEXHTa AE-I [8-321] (C145A, C40A/C85A) (SEQ ID NO: 35), and pPROEXHTa AE-I (1-321] (C40A/C85A, C252A/C274A) (SEQ ID NO: 37) into *E. coli* and their Expression Using the plasmids of the amidating enzyme and its derivatives, *E. coli* JM109 was transformed. The transformed *E. coli* was cultured in about 1 liter of the LB medium (0.5% (w/v) yeast extract, 1% (w/v) tryptone, 0.5% (w/v) NaCl) under shaking at 37° C., and the expression was induced by the addition of isopropyl-β-D-thiogalactoside (IPTG). After the induction of expression, culturing was continued for about 12-16 hours. The cells obtained were disrupted, and after centrifugation the precipitate fraction containing the inclusion body was recovered. By washing the precipitate with a Triton X-100 (detergent)-containing buffer, the proteins and membrane components derived from JM109 were removed to recover the inclusion bodies of the amidating enzyme and its derivatives. The expression and purity of the amidating enzyme and its derivatives were confirmed by SDS-PAGE (see FIG. 6). The expression level was determined by the UV method after solubilizing the inclusion body with a denaturing agent.

To the *E. coli* JM109 that was made competent, each of expression vectors (pPROEXHTa AE-I [1-321] (SEQ ID NO: 2), pPROEXHTa AE-I [8-321] (C145A) (SEQ ID NO: 25), pPROEXHTa AE-I [1-321] (C40A/C85A) (SEQ ID NO: 27), pPROEXHTa AE-I [1-321] (C73A/C90A) (SEQ ID NO: 29), pPROEXHTa AE-I [1-321] (C186A/C293A) (SEQ ID NO: 31), pPROEXHTa AE-I [1-321] (C252A/C274A) (SEQ ID NO: 33), pPROEXHTa AE-I [8-321] (C145A, C40A/C85A) (SEQ ID NO: 35), and pPROEXHTa AE-I [1-321] (C40A/C85A, C252A/C274A) (SEQ ID NO: 37)) created in Working Examples 1 and 2 was added. After incubating on ice for 10 minutes, they were inoculated into a LB-agar medium (0.5% (w/v) yeast extract, 1% (w/v) tryptone, 0.5% (w/v) NaCl, 1.5% (w/v) agar) containing 10 μg/mL ampicillin (antibiotics), and incubated overnight at 37° C. to obtain the colonies of transformants JM109[pPROEXHTa AE-I [1-321] (SEQ ID NO: 2)], JM109[pPROEXHTa AE-I [8-321] (C145A) (SEQ ID NO: 25)], JM109[pPROEXHTa AE-I [1-321] (C40A/C85A) (SEQ ID NO: 27)], JM109[pPROEXHTa AE-I [1-321] (C73A/C90A) (SEQ ID NO: 29)], JM109-[pPROEXHTa AE-I [1-321] (C186A/C293A) (SEQ ID NO: 31)], JM109[pPROEXHTa AE-I [1-321] (C252A/C274A) (SEQ ID NO: 33)], JM109[pPROEXHTa AE-I [8-321] (C145A, C40A/C85A) (SEQ ID NO: 35)], and JM109 [pPROEXHTa AE-I [1-321] (C40A/C85A), C252A/C274A) (SEQ ID NO: 37) of respective derivatives.

Colonies of these transformants were each inoculated into a test tube containing 5 mL of the LB medium (0.5% (w/v) yeast extract, 1% (w/v) tryptone, 0.5% (w/v) NaCl) containing 10 μg/mL ampicillin (antibiotics), and cultured under shaking at 37° C. for about 12-16 hours. The entire volume of the culture liquid was inoculated into 1 liter of the LB medium containing 10 μg/mL ampicillin and cultured under shaking at 37° C. At 3-6 hours after culturing (when OD660 nM reached 0.5-0.8), IPTG was added to a final concentration of 1 mM to induce expression.

Since the C-terminal α-amidating enzyme and its derivatives are intracellularly expressed as insoluble inclusion bodies, the inclusion bodies were recovered in the following manner. The cells were recovered by centrifuging (6000 rpm, 4° C.) 1 liter of the culture liquid for 10 minutes, suspended in 100 mL of water, and then the cells were disrupted by French press (10,000 psi; twice). The cell-disrupted liquid was centrifuged for 15 minutes (6000 rpm, 4° C.), and the inclusion body of interest was transferred to the precipitate fraction. Since this procedure transfers most of the protein derived from the host *E. coli* JM109 migrates to the supernatant, said protein can be removed. Then, the precipitate fraction was suspended in 50 mL of 100 mM Tris-HCl buffer, pH 7.0, containing 1% (w/w) Triton X-100 (detergent), and centrifuged (6000 rpm, 4° C.) for 15 minutes to recover the precipitate (thus, the membrane components etc. derived from JM109 is dissolved in the detergent and migrated to the supernatant, said membrane components etc. can be removed). By repeating this procedure twice, the inclusion body of the C-terminal α-amidating enzyme was recovered, which was finally suspended into 1 mL of 100 mM Tris-HCl buffer, pH 7.0, containing 1% (w/w) Triton X-100 (detergent) to obtain an inclusion body suspension.

Figure 6:
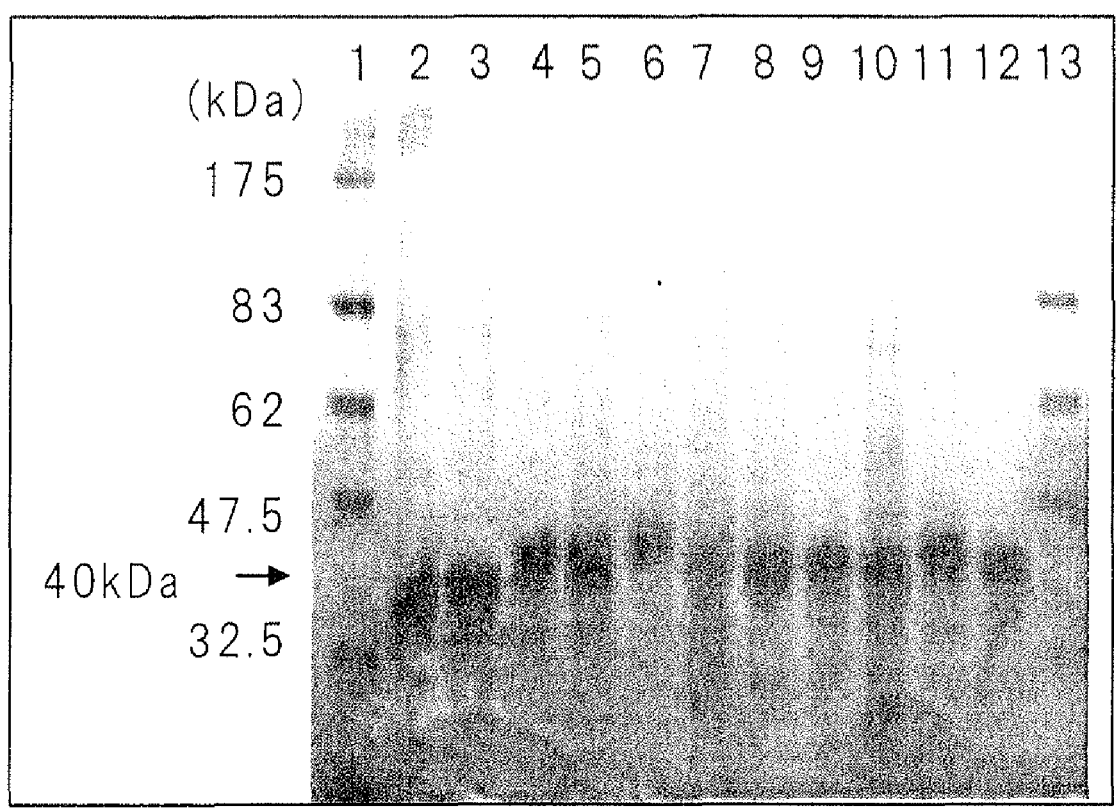
FIG. 6 shows the result of confirming the expression of the amidating enzyme and derivatives thereof by SDS-PAGE. Each lane is as follows.

The inclusion body suspensions (10 µl) obtained of each derivative was diluted 2-fold with 10 µl of a sample buffer (2M urea, 375 mM Tris-HCl, pH 6.8, 30% (v/v) glycerol, 7% (w/v) SDS, 15% (v/v) 2-mercaptoethanol, 0.1% (w/v) bromophenol blue) for SDS-PAGE, and a 0.1 µl aliquot (corresponding to 1-10 µg portion) was subjected to a 10% SDS-PAGE gel to confirm the expression and purity (see FIG. 6). In the C-terminal α-amidating enzyme and all of its derivatives, a band was detected at a molecular weight of about 40 kDa, and the purity was about 70-90%.

The inclusion body suspensions (10 µl) of the amidating enzyme and all of its derivatives were solubilized with 10 mL of a denaturing agent (8M urea), and absorbance A at a wavelength of 280 nm was measured by a spectrophotometer to calculate the concentration C based on the Lambert-Beer's law according to the following equation:

Concentration $C(mg/mL) = A \cdot Mw/\kappa d$ wherein, A is absorbance at a wavelength of 280 nm, Mw is molecular weight (about 45,000 Da), and κd is extinction coefficient (41,700 ($M^{-1} \cdot cm^{-1}$); The C-terminal α-amidating enzyme and derivatives include 3 and 21 amino acids of tryptophan (extinction coefficient 5500) and tyrosine (extinction coefficient 1200), respectively.

Based on the concentration C thus calculated, the expression levels of the proteins of the amidating enzyme and its derivatives were calculated to be 100-160 mg/liter of the medium.

Working Example 4

Refolding and Assessment of Enzyme Activity of the Amidating Enzyme AE-I [1-321] (SEQ ID NO: 2) and its derivatives AE-I [8-321] (C145A) (SEQ ID NO: 25), AE-I [1-321] (C40A/C85A) (SEQ ID NO: 27), AE-I [1-321] (C73A/C90A) (SEQ ID NO: 29), AE-I [1-321] (C186A/C293A) (SEQ ID NO: 31), AE-I [1-321] (C252A/C274A) (SEQ ID NO: 33), AE-I [8-321] (C145A, C40A/C85A) (SEQ ID NO: 35), and AE-I [1-321] (C40A/C85A, C252A/C274A) (SEQ ID NO: 37)

Using the inclusion bodies of the amidating enzyme and its derivatives obtained in Working Example 3, the refolding procedure was carried out by denaturing them with a 8M urea buffer having a denaturing effect and then by diluting with a denaturant-free buffer. Since the denaturing agent remains in the refolding solution obtained, it was removed by dialysis. Denaturing is known to inhibit the measurement of enzyme activity. For the dialyzed samples obtained, C-terminal α-amidating enzyme activity was assessed.

One mL of the inclusion bodies of the C-terminal α-amidating enzyme and its derivatives obtained in Working Example 3 were solubilized to a final concentration of 2.4 g/L with 8M urea, 50 mM Tris-HCl (pH 10.0 at 15° C.), and 50 mM NaCl. The solution was incubated at 15° C. for 2-4 days to break down S—S bonds.

Then, the denaturant concentration was lowered by diluting 8-fold with 50 mM Tris-HCl (pH 8.0 at 4° C.) and 50 mM NaCl to facilitate regeneration of conformation (refolding procedure). Furthermore, since urea is known to inhibit the measurement of activity, dialysis was performed overnight with 500 mL of 50 mM Tris-HCl (pH 8.0 at 4° C.) and 50 mM NaCl at 4° C. The dialysis membrane used was SPECTRUM's SPECTRA/Por 2 MWCO: 12-14,000 Da.

After refolding, the concentration of the protein obtained for the solution after dialysis was determined by absorbance at 280 nm in a manner similar to that in Working Example 3 (see FIG. 7). For the measurement of enzyme activity of the C-terminal α-amidating enzyme or its derivatives, the conversion of a synthetic substrate [$^{125}$I]-Ac-Tyr-Phe-Gly to [$^{125}$I]-Ac-Tyr-Phe-NH$_2$ was utilized. The method of determining C-terminal α-amidating enzyme activity and the definition of Unit are as described above.

FIG. 7 shows the result of determining the enzyme activity of the C-terminal α-amidating enzyme and its derivatives. The enzyme activity U per mg of protein is as follows: AE-I [1-321] (SEQ ID NO: 2): 205 U/mg, AE-I [8-321] (C145A) (SEQ ID NO: 25): 840 U/mg, AE-I [1-321] (C40A/C85A) (SEQ ID NO: 27): 1798 U/mg, AE-I [1-321] (C73A/C90A) (SEQ ID NO: 29): 56 U/mg, AE-I [1-321] (C186A/C293A) (SEQ ID NO: 31): ND U/mg, AE-I [1-321] (C252A/C274A) (SEQ ID NO: 33): 271 U/mg, AE-I [8-321] (C145A, C40A/C85A) (SEQ ID NO: 35): 778 U/mg, and AE-I [1-321] (C40A/C85A, C252A/C274A) (SEQ ID NO: 37): 2260 U/mg. As a result, compared to the wild type AE-I [1-321] (SEQ ID NO: 2) in which no S—S bonds have been removed, a low enzyme activity was exhibited by AE-I [1-321] (C73A/C90A) (SEQ ID NO: 29) and AE-I [1-321] (C186A/C293A) (SEQ ID NO: 31), and in AE-I [1-321] (C186A/C293A) (SEQ ID NO: 31) among others, no enzyme activity was detected. In other words, it was suggested that the S—S bond formed between $^{186}$Cys-$^{293}$Cys be important in the activity expression of an amidating enzyme.

On the other hand, compared to the wild type AE-I [1-321] (SEQ ID NO: 2) in which no S—S bonds have been removed, a high enzyme activity was exhibited by AE-I [8-321] (C145A) (SEQ ID NO: 25), AE-I [1-321] (C40A/C85A) (SEQ ID NO: 27) and AE-I [1-321] (C252A/C274A) (SEQ ID NO: 33) in which one pair of S—S bond has been removed, as well as AE-I [8-321] (C145A, C40A/C85A) (SEQ ID NO: 35) and AE-I [1-321] (C40A/C85A, C252A/ C274A) (SEQ ID NO: 37) in which two pairs of S—S bonds have been removed. Among them, AE-I [8-321] (C145A) (SEQ ID NO: 25) and AE-I [1-321] (C40A/C85A) (SEQ ID NO: 27) exhibited the enzyme activity about 4-fold and about 9-fold higher, respectively, compared to the wild type, and AE-I [1-321] (C40A/C85A, C252A/C274A) (SEQ ID NO: 37) exhibited the enzyme activity as high as about 11-fold.

The enzyme activity per mL of the culture liquid for these five derivatives was calculated to be (in the calculation, the mean expression level was assumed to be 130 mg/L of the culture medium): AE-I [1-321] (SEQ ID NO: 2): 27 U/mL, AE-I [8-321](C145A) (SEQ ID NO: 25): 109 U/mL, AE-I [1-321] (C40A/C85A) (SEQ ID NO: 27): 234 U/mL, AE-I [1-321] (C252A/C274A) (SEQ ID NO: 33): 35 U/mL, AE-I [8-321] (C145A, C40A/C85A) (SEQ ID NO: 35): 101 U/mL, and AE-I [1-321] (C40A/C85A, C252A/C293A) (SEQ ID NO: 37): 294 U/mL.

In the invention described in Kokai (Japanese Unexamined Patent Publication) No. 7-250691, the activity of the amidating enzyme recombinantly produced using *E. coli* was about 10-15 mU per mL of the culture liquid. In contrast, the enzyme activity of the derivatives obtained in the above method of the present invention was about 35-300 U/mL as described above. Though simple comparison may be not applicable because of differences in the expression level of the enzyme and the method of refolding, the enzyme activity was enhanced by about 2,000-30,000 fold compared to that of the amidating enzyme obtained in the invention described in Kokai (Japanese Unexamined Patent Publication) No. 7-250691.

It has been confirmed that with regard to the culturing of the C-terminal α-amidating enzyme derivative of the present invention, a high-density culture can lead to the expression level of said derivative at about 5-10 g/L. In this case, the enzyme activity finally obtained may be calculated to be about 23,000 U per mL of the culture liquid at the maximum, which far exceeds the enzyme activity (an enzyme activity of 2,860 U per mL of the culture liquid) obtained for the enzyme recombinantly produced using CHO cells in the invention described in Kokai (Japanese Unexamined Patent Publication) No. 7-163340.

In accordance with the present invention, a recombinant C-terminal α-amidating enzyme derivative was obtained having a very high enzyme activity compared to the enzyme activity per mL of the culture liquid attained in the conventional technology (see Kokai (Japanese Unexamined Patent Publication) No. 7-250691) in the production of an amidating enzyme using E. coli. In accordance with the present invention furthermore, a recombinant C-terminal α-amidating enzyme derivative was obtained having a high enzyme activity compared to the enzyme activity attained in a gene recombinant technology (see Kokai (Japanese Unexamined Patent Publication) No. 7-163340) using CHO cells. Since the method claimed in the present invention uses E. coli, it can produce said amidating enzyme in a short period of time and its productivity is very high compared to the above CHO cell-culturing method.

It has also been confirmed that the C-terminal α-amidating enzyme of the present invention amidates glucagon like peptide-1 (GLP-1) precursor (Gly is added to the C-terminal) in vitro, which indicates that the recombinant C-terminal α-amidating enzyme of the present invention can be fully used in the amidation reaction for the production of C-terminal α-amidated peptides.

INDUSTRIAL APPLICABILITY

The present invention can provide a recombinant C-terminal α-amidating enzyme derivative having an enzyme activity higher than the conventional enzymes recombinantly produced using E. coli.

What is claimed is:

1. A recombinant enzyme comprising:

a polypeptide having an amino acid sequence set forth in SEQ ID NO: 2 wherein at least one cysteine residue at positions 6, 145, 40, 85, 252, or 274 is substituted to a non-cysteine amino acid, and wherein said recombinant enzyme has α-amidating activity and lacks at least one disulfide bond between positions 6 and 145, positions 40 and 85, or positions 252 and 274.

2. A recombinant enzyme comprising:

a polypeptide having an amino acid sequence set forth in SEQ ID NO: 2 wherein at least one cysteine residue at positions 6, 145, 40, 85, 252, or 274 is substituted to a non-cysteine amino acid, and wherein said recombinant enzyme has α-amidating activity and lacks at least one disulfide bond between positions 6 and 145, positions 40 and 85, or positions 252 and 274; and wherein said non-cysteine amino acid is alanine.

3. The recombinant enzyme of claim 2, wherein said enzyme is AE-I [1-321] (C40A and C85A) (SEQ ID NO: 27), AE-I [1-321] (C252A and C274A) (SEQ ID NO: 33), AE-I [1-321] (C40A and C85A, C252A and C274A) (SEQ ID NO: 37), AE-I [8-321] (C145A) (SEQ ID NO: 25), or AE-I [8-321] (C145A, C40A, and C85A) (SEQ ID NO: 35).

* * * * *

SEQUENCE LISTING

```
<160> NUMBER OF SEQ ID NOS: 40

<210> SEQ ID NO 1
<211> LENGTH: 1050
<212> TYPE: DNA
<213> ORGANISM: Xenopus leavis
<220> FEATURE:
<223> OTHER INFORMATION: AE-I[1-321]
<220> FEATURE:
<221> NAME/KEY: CDS
<222> LOCATION: (85)..(1047)

<400> SEQUENCE: 1
atgtcgtact accatcacca tcaccatcac gattacgata tcccaacgac cgaaaacctg         60
tattttcagg gcgccatgga tccg tca ctt tcc aat gac tgc ttg gga acc          111
                          Ser Leu Ser Asn Asp Cys Leu Gly Thr
                           1               5 acg cgg ccc gtt atg tct cca ggc tca tca gat tat act cta gat atc         159
Thr Arg Pro Val Met Ser Pro Gly Ser Ser Asp Tyr Thr Leu Asp Ile
 10              15                  20                  25 cgc atg cca gga gta act ccg aca gag tcg gac aca tat ttg tgc aag         207
Arg Met Pro Gly Val Thr Pro Thr Glu Ser Asp Thr Tyr Leu Cys Lys
                 30                  35                  40 tct tac cgg ctg cca gtg gat gat gaa gcc tat gta gtt gac ttc aga         255
Ser Tyr Arg Leu Pro Val Asp Asp Glu Ala Tyr Val Val Asp Phe Arg
             45                  50                  55 cca cat gcc aat atg gat act gca cat cac atg ctt cta ttt gga tgc         303
Pro His Ala Asn Met Asp Thr Ala His His Met Leu Leu Phe Gly Cys
         60                  65                  70 aat ata cct tct tcc act gat gat tac tgg gac tgt agt gcg gga act         351
Asn Ile Pro Ser Ser Thr Asp Asp Tyr Trp Asp Cys Ser Ala Gly Thr
     75                  80                  85 tgc atg gac aaa tcc agt ata atg tat gcc tgg gca aag aat gca cca         399
Cys Met Asp Lys Ser Ser Ile Met Tyr Ala Trp Ala Lys Asn Ala Pro
 90                  95                 100                 105 ccc acc aaa ctt cca gaa gga gtt ggc ttt cgt gtt gga ggg aaa tca         447
Pro Thr Lys Leu Pro Glu Gly Val Gly Phe Arg Val Gly Gly Lys Ser
                110                 115                 120 ggc agt aga tat ttt gtg ctt caa gtt cac tat gga aat gtg aaa gca         495
```

```
Gly Ser Arg Tyr Phe Val Leu Gln Val His Tyr Gly Asn Val Lys Ala
            125                 130                 135 ttc cag gat aaa cat aaa gat tgc acg ggg gtg aca gta cga gta aca      543
Phe Gln Asp Lys His Lys Asp Cys Thr Gly Val Thr Val Arg Val Thr
            140                 145                 150 cct gaa aaa caa ccg caa att gca ggc att tat ctt tca atg tct gtg      591
Pro Glu Lys Gln Pro Gln Ile Ala Gly Ile Tyr Leu Ser Met Ser Val
            155                 160                 165 gac act gtt att cca cct ggg gaa gag gca gtt aat tct gat atc gcc      639
Asp Thr Val Ile Pro Pro Gly Glu Glu Ala Val Asn Ser Asp Ile Ala
170                 175                 180                 185 tgc ctc tac aac agg ccg aca ata cac cca ttt gcc tac aga gtc cac      687
Cys Leu Tyr Asn Arg Pro Thr Ile His Pro Phe Ala Tyr Arg Val His
            190                 195                 200 act cat cag ttg ggg cag gtc gta agt gga ttt aga gtg aga cat ggc      735
Thr His Gln Leu Gly Gln Val Val Ser Gly Phe Arg Val Arg His Gly
            205                 210                 215 aag tgg tct tta att ggt aga caa agc cca cag ctg cca cag gca ttt      783
Lys Trp Ser Leu Ile Gly Arg Gln Ser Pro Gln Leu Pro Gln Ala Phe
            220                 225                 230 tac cct gta gag cat cca gta gag att agc cct ggg gat att ata gca      831
Tyr Pro Val Glu His Pro Val Glu Ile Ser Pro Gly Asp Ile Ile Ala
            235                 240                 245 acc agg tgt ctg ttc act ggt aaa ggc agg acg tca gca aca tat att      879
Thr Arg Cys Leu Phe Thr Gly Lys Gly Arg Thr Ser Ala Thr Tyr Ile
250                 255                 260                 265 ggt ggc aca tct aac gat gaa atg tgt aat tta tac atc atg tat tac      927
Gly Gly Thr Ser Asn Asp Glu Met Cys Asn Leu Tyr Ile Met Tyr Tyr
            270                 275                 280 atg gat gcg gcc cat gct acg tca tac atg acc tgt gta cag acg ggt      975
Met Asp Ala Ala His Ala Thr Ser Tyr Met Thr Cys Val Gln Thr Gly
            285                 290                 295 gaa cca aag tta ttt caa aac atc cct gag att gca aat gtt ccc att     1023
Glu Pro Lys Leu Phe Gln Asn Ile Pro Glu Ile Ala Asn Val Pro Ile
            300                 305                 310 cct gta agc cct gac atg atg atg taa                                 1050
Pro Val Ser Pro Asp Met Met Met
            315                 320

<210> SEQ ID NO 2
<211> LENGTH: 321
<212> TYPE: PRT
<213> ORGANISM: Xenopus leavis
<220> FEATURE:
<223> OTHER INFORMATION: AE-I[1-321]

<400> SEQUENCE: 2

Ser Leu Ser Asn Asp Cys Leu Gly Thr Thr Arg Pro Val Met Ser Pro
1               5                   10                  15

Gly Ser Ser Asp Tyr Thr Leu Asp Ile Arg Met Pro Gly Val Thr Pro
                20                  25                  30

Thr Glu Ser Asp Thr Tyr Leu Cys Lys Ser Tyr Arg Leu Pro Val Asp
            35                  40                  45

Asp Glu Ala Tyr Val Val Asp Phe Arg Pro His Ala Asn Met Asp Thr
50                  55                  60

Ala His His Met Leu Leu Phe Gly Cys Asn Ile Pro Ser Ser Thr Asp
65                  70                  75                  80

Asp Tyr Trp Asp Cys Ser Ala Gly Thr Cys Met Asp Lys Ser Ser Ile
                85                  90                  95

Met Tyr Ala Trp Ala Lys Asn Ala Pro Pro Thr Lys Leu Pro Glu Gly
```

```
                100             105                 110
Val Gly Phe Arg Val Gly Lys Ser Gly Ser Arg Tyr Phe Val Leu
        115                 120                 125

Gln Val His Tyr Gly Asn Val Lys Ala Phe Gln Asp Lys His Lys Asp
        130                 135                 140

Cys Thr Gly Val Thr Val Arg Val Thr Pro Glu Lys Gln Pro Gln Ile
145                 150                 155                 160

Ala Gly Ile Tyr Leu Ser Met Ser Val Asp Thr Val Ile Pro Pro Gly
                165                 170                 175

Glu Glu Ala Val Asn Ser Asp Ile Ala Cys Leu Tyr Asn Arg Pro Thr
                180                 185                 190

Ile His Pro Phe Ala Tyr Arg Val His Thr His Gln Leu Gly Gln Val
        195                 200                 205

Val Ser Gly Phe Arg Val Arg His Gly Lys Trp Ser Leu Ile Gly Arg
        210                 215                 220

Gln Ser Pro Gln Leu Pro Gln Ala Phe Tyr Pro Val Glu His Pro Val
225                 230                 235                 240

Glu Ile Ser Pro Gly Asp Ile Ile Ala Thr Arg Cys Leu Phe Thr Gly
                245                 250                 255

Lys Gly Arg Thr Ser Ala Thr Tyr Ile Gly Gly Thr Ser Asn Asp Glu
                260                 265                 270

Met Cys Asn Leu Tyr Ile Met Tyr Tyr Met Asp Ala Ala His Ala Thr
        275                 280                 285

Ser Tyr Met Thr Cys Val Gln Thr Gly Glu Pro Lys Leu Phe Gln Asn
        290                 295                 300

Ile Pro Glu Ile Ala Asn Val Pro Ile Pro Val Ser Pro Asp Met Met
305                 310                 315                 320

Met

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      AEp003 oligonucleotide

<400> SEQUENCE: 3
attggatccg ggaaccacgc ggcc                                          24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp004 oligonucleotide

<400> SEQUENCE: 4 tcaccccgt ggcatcttta tgt                                            23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp005 oligonucleotide

<400> SEQUENCE: 5
```
acataaagat gccacggggg tga                                    23

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      AEp006 oligonucleotide

<400> SEQUENCE: 6
tgcctcgagt tacatcatca tgtcagggct                             30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      AEp007 oligonucleotide

<400> SEQUENCE: 7
attggatccg tcactttcca atgactgctt                             30

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp008 oligonucleotide

<400> SEQUENCE: 8
ggtaagactt ggccaaatat gtg                                    23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp009 oligonucleotide

<400> SEQUENCE: 9
cacatatttg gccaagtctt acc                                    23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp010 oligonucleotide

<400> SEQUENCE: 10
ttcccgcact agcgtcccag taa                                    23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp011 oligonucleotide

<400> SEQUENCE: 11
ttactgggac gctagtgcgg gaa                                    23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp012 oligonucleotide

<400> SEQUENCE: 12
aaggtatatt ggctccaaat aga                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp013 oligonucleotide

<400> SEQUENCE: 13
tctatttgga gccaatatac ctt                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp014 oligonucleotide

<400> SEQUENCE: 14
atttgtccat ggcagttccc gca                                              23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp015 oligonucleotide

<400> SEQUENCE: 15
tgcgggaact gccatggaca aat                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp016 oligonucleotide

<400> SEQUENCE: 16
tgttgtagag ggcggcgata tca                                              23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp017 oligonucleotide

<400> SEQUENCE: 17
tgatatcgcc gccctctaca aca                                              23

<210> SEQ ID NO 18

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp018 oligonucleotide

<400> SEQUENCE: 18
ccgtctgtac agcggtcatg tat                                              23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp019 oligonucleotide

<400> SEQUENCE: 19
atacatgacc gctgtacaga cgg                                              23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp020 oligonucleotide

<400> SEQUENCE: 20
cagtgaacag agccctggtt gct                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp021 oligonucleotide

<400> SEQUENCE: 21
agcaaccagg gctctgttca ctg                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp022 oligonucleotide

<400> SEQUENCE: 22
tgtataaatt agccatttca tcg                                              23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      AEp023 oligonucleotide

<400> SEQUENCE: 23
cgatgaaatg gctaatttat aca                                              23

<210> SEQ ID NO 24
<211> LENGTH: 1029
<212> TYPE: DNA
```

-continued

```
<213> ORGANISM: Artificial Sequence
<220> FEATURE:
<223> OTHER INFORMATION: Description of Artificial Sequence: Synthetic
      AE-I[8-321]C145A polynucleotide
<220> FEATURE:
<221> NAME/KEY: CDS
<222> LOCATION: (85)..(1026)

<400> SEQUENCE: 24
atgtcgtact accatcacca tcaccatcac gattacgata tcccaacgac cgaaaacctg      60
tattttcagg gcgccatgga tccg gga acc acg cgg ccc gtt atg tct cca         111
                           Gly Thr Thr Arg Pro Val Met Ser Pro
                             1               5 ggc tca tca gat tat act cta gat atc cgc atg cca gga gta act ccg        159
Gly Ser Ser Asp Tyr Thr Leu Asp Ile Arg Met Pro Gly Val Thr Pro
 10              15                  20                  25 aca gag tcg gac aca tat ttg tgc aag tct tac cgg ctg cca gtg gat        207
Thr Glu Ser Asp Thr Tyr Leu Cys Lys Ser Tyr Arg Leu Pro Val Asp
                 30                  35                  40 gat gaa gcc tat gta gtt gac ttc aga cca cat gcc aat atg gat act        255
Asp Glu Ala Tyr Val Val Asp Phe Arg Pro His Ala Asn Met Asp Thr
             45                  50                  55 gca cat cac atg ctt cta ttt gga tgc aat ata cct tct tcc act gat        303
Ala His His Met Leu Leu Phe Gly Cys Asn Ile Pro Ser Ser Thr Asp
         60                  65                  70 gat tac tgg gac tgt agt gcg gga act tgc atg gac aaa tcc agt ata        351
Asp Tyr Trp Asp Cys Ser Ala Gly Thr Cys Met Asp Lys Ser Ser Ile
     75                  80                  85 atg tat gcc tgg gca aag aat gca cca ccc acc aaa ctt cca gaa gga        399
Met Tyr Ala Trp Ala Lys Asn Ala Pro Pro Thr Lys Leu Pro Glu Gly
 90                  95                 100                 105 gtt ggc ttt cgt gtt gga ggg aaa tca ggc agt aga tat ttt gtg ctt        447
Val Gly Phe Arg Val Gly Gly Lys Ser Gly Ser Arg Tyr Phe Val Leu
                110                 115                 120 caa gtt cac tat gga aat gtg aaa gca ttc cag gat aaa cat aaa gat        495
Gln Val His Tyr Gly Asn Val Lys Ala Phe Gln Asp Lys His Lys Asp
            125                 130                 135 gcc acg ggg gtg aca gta cga gta aca cct gaa aaa caa ccg caa att        543
Ala Thr Gly Val Thr Val Arg Val Thr Pro Glu Lys Gln Pro Gln Ile
        140                 145                 150 gca ggc att tat ctt tca atg tct gtg gac act gtt att cca cct ggg        591
Ala Gly Ile Tyr Leu Ser Met Ser Val Asp Thr Val Ile Pro Pro Gly
    155                 160                 165 gaa gag gca gtt aat tct gat atc gcc tgc ctc tac aac agg ccg aca        639
Glu Glu Ala Val Asn Ser Asp Ile Ala Cys Leu Tyr Asn Arg Pro Thr
170                 175                 180                 185 ata cac cca ttt gcc tac aga gtc cac act cat cag ttg ggg cag gtc        687
Ile His Pro Phe Ala Tyr Arg Val His Thr His Gln Leu Gly Gln Val
                190                 195                 200 gta agt gga ttt aga gtg aga cat ggc aag tgg tct tta att ggt aga        735
Val Ser Gly Phe Arg Val Arg His Gly Lys Trp Ser Leu Ile Gly Arg
            205                 210                 215 caa agc cca cag ctg cca cag gca ttt tac cct gta gag cat cca gta        783
Gln Ser Pro Gln Leu Pro Gln Ala Phe Tyr Pro Val Glu His Pro Val
        220                 225                 230 gag att agc cct ggg gat att ata gca acc agg tgt ctg ttc act ggt        831
Glu Ile Ser Pro Gly Asp Ile Ile Ala Thr Arg Cys Leu Phe Thr Gly
    235                 240                 245 aaa ggc agg acg tca gca aca tat att ggt ggc aca tct aac gat gaa        879
Lys Gly Arg Thr Ser Ala Thr Tyr Ile Gly Gly Thr Ser Asn Asp Glu
250                 255                 260                 265
```

```
atg tgt aat tta tac atc atg tat tac atg gat gcg gcc cat gct acg    927
Met Cys Asn Leu Tyr Ile Met Tyr Tyr Met Asp Ala Ala His Ala Thr
            270             275             280 tca tac atg acc tgt gta cag acg ggt gaa cca aag tta ttt caa aac    975
Ser Tyr Met Thr Cys Val Gln Thr Gly Glu Pro Lys Leu Phe Gln Asn
        285             290             295 atc cct gag att gca aat gtt ccc att cct gta agc cct gac atg atg   1023
Ile Pro Glu Ile Ala Asn Val Pro Ile Pro Val Ser Pro Asp Met Met
        300             305             310 atg taa                                                            1029
Met
```

<210> SEQ ID NO 25
<211> LENGTH: 314
<212> TYPE: PRT
<213> ORGANISM: Artificial Sequence
<220> FEATURE:
<223> OTHER INFORMATION: Description of Artificial Sequence: Synthetic
      AE-I[8-321]C145A polypeptide

<400> SEQUENCE: 25

```
Gly Thr Thr Arg Pro Val Met Ser Pro Gly Ser Ser Asp Tyr Thr Leu
1               5                   10                  15

Asp Ile Arg Met Pro Gly Val Thr Pro Thr Glu Ser Asp Thr Tyr Leu
            20                  25                  30

Cys Lys Ser Tyr Arg Leu Pro Val Asp Asp Glu Ala Tyr Val Val Asp
        35                  40                  45

Phe Arg Pro His Ala Asn Met Asp Thr Ala His His Met Leu Leu Phe
    50                  55                  60

Gly Cys Asn Ile Pro Ser Ser Thr Asp Tyr Trp Asp Cys Ser Ala
65                  70                  75                  80

Gly Thr Cys Met Asp Lys Ser Ser Ile Met Tyr Ala Trp Ala Lys Asn
                85                  90                  95

Ala Pro Pro Thr Lys Leu Pro Glu Gly Val Gly Phe Arg Val Gly Gly
            100                 105                 110

Lys Ser Gly Ser Arg Tyr Phe Val Leu Gln Val His Tyr Gly Asn Val
        115                 120                 125

Lys Ala Phe Gln Asp Lys His Lys Asp Ala Thr Gly Val Thr Val Arg
    130                 135                 140

Val Thr Pro Glu Lys Gln Pro Gln Ile Ala Gly Ile Tyr Leu Ser Met
145                 150                 155                 160

Ser Val Asp Thr Val Ile Pro Pro Gly Glu Glu Ala Val Asn Ser Asp
                165                 170                 175

Ile Ala Cys Leu Tyr Asn Arg Pro Thr Ile His Pro Phe Ala Tyr Arg
            180                 185                 190

Val His Thr His Gln Leu Gly Gln Val Val Ser Gly Phe Arg Val Arg
        195                 200                 205

His Gly Lys Trp Ser Leu Ile Gly Arg Gln Ser Pro Gln Leu Pro Gln
    210                 215                 220

Ala Phe Tyr Pro Val Glu His Pro Val Glu Ile Ser Pro Gly Asp Ile
225                 230                 235                 240

Ile Ala Thr Arg Cys Leu Phe Thr Gly Lys Gly Arg Thr Ser Ala Thr
                245                 250                 255

Tyr Ile Gly Gly Thr Ser Asn Asp Glu Met Cys Asn Leu Tyr Ile Met
            260                 265                 270

Tyr Tyr Met Asp Ala Ala His Ala Thr Ser Tyr Met Thr Cys Val Gln
        275                 280                 285
```

-continued

```
Thr Gly Glu Pro Lys Leu Phe Gln Asn Ile Pro Glu Ile Ala Asn Val
    290                 295                 300
Pro Ile Pro Val Ser Pro Asp Met Met Met
305                 310

<210> SEQ ID NO 26
<211> LENGTH: 1050
<212> TYPE: DNA
<213> ORGANISM: Artificial Sequence
<220> FEATURE:
<223> OTHER INFORMATION: Description of Artificial Sequence: Synthetic
      AE-I[1-321]C40A,C85A polynucleotide
<220> FEATURE:
<221> NAME/KEY: CDS
<222> LOCATION: (85)..(1047)

<400> SEQUENCE: 26
atgtcgtact accatcacca tcaccatcac gattacgata tcccaacgac cgaaaacctg      60
tattttcagg gcgccatgga tccg tca ctt tcc aat gac tgc ttg gga acc       111
                          Ser Leu Ser Asn Asp Cys Leu Gly Thr
                            1               5 acg cgg ccc gtt atg tct cca ggc tca tca gat tat act cta gat atc      159
Thr Arg Pro Val Met Ser Pro Gly Ser Ser Asp Tyr Thr Leu Asp Ile
 10              15                  20                  25 cgc atg cca gga gta act ccg aca gag tcg gac aca tat ttg gcc aag      207
Arg Met Pro Gly Val Thr Pro Thr Glu Ser Asp Thr Tyr Leu Ala Lys
             30                  35                  40 tct tac cgg ctg cca gtg gat gat gaa gcc tat gta gtt gac ttc aga      255
Ser Tyr Arg Leu Pro Val Asp Asp Glu Ala Tyr Val Val Asp Phe Arg
         45                  50                  55 cca cat gcc aat atg gat act gca cat cac atg ctt cta ttt gga tgc      303
Pro His Ala Asn Met Asp Thr Ala His His Met Leu Leu Phe Gly Cys
     60                  65                  70 aat ata cct tct tcc act gat gat tac tgg gac gct agt gcg gga act      351
Asn Ile Pro Ser Ser Thr Asp Asp Tyr Trp Asp Ala Ser Ala Gly Thr
 75                  80                  85 tgc atg gac aaa tcc agt ata atg tat gcc tgg gca aag aat gca cca      399
Cys Met Asp Lys Ser Ser Ile Met Tyr Ala Trp Ala Lys Asn Ala Pro
 90                  95                 100                 105 ccc acc aaa ctt cca gaa gga gtt ggc ttt cgt gtt gga ggg aaa tca      447
Pro Thr Lys Leu Pro Glu Gly Val Gly Phe Arg Val Gly Gly Lys Ser
             110                 115                 120 ggc agt aga tat ttt gtg ctt caa gtt cac tat gga aat gtg aaa gca      495
Gly Ser Arg Tyr Phe Val Leu Gln Val His Tyr Gly Asn Val Lys Ala
         125                 130                 135 ttc cag gat aaa cat aaa gat tgc acg ggg gtg aca gta cga gta aca      543
Phe Gln Asp Lys His Lys Asp Cys Thr Gly Val Thr Val Arg Val Thr
     140                 145                 150 cct gaa aaa caa ccg caa att gca ggc att tat ctt tca atg tct gtg      591
Pro Glu Lys Gln Pro Gln Ile Ala Gly Ile Tyr Leu Ser Met Ser Val
 155                 160                 165 gac act gtt att cca cct ggg gaa gag gca gtt aat tct gat atc gcc      639
Asp Thr Val Ile Pro Pro Gly Glu Glu Ala Val Asn Ser Asp Ile Ala
170                 175                 180                 185 tgc ctc tac aac agg ccg aca ata cac cca ttt gcc tac aga gtc cac      687
Cys Leu Tyr Asn Arg Pro Thr Ile His Pro Phe Ala Tyr Arg Val His
             190                 195                 200 act cat cag ttg ggg cag gtc gta agt gga ttt aga gtg aga cat ggc      735
Thr His Gln Leu Gly Gln Val Val Ser Gly Phe Arg Val Arg His Gly
         205                 210                 215 aag tgg tct tta att ggt aga caa agc cca cag ctg cca cag gca ttt      783
Lys Trp Ser Leu Ile Gly Arg Gln Ser Pro Gln Leu Pro Gln Ala Phe
```

```
                   220                 225                 230
tac cct gta gag cat cca gta gag att agc cct ggg gat att ata gca       831
Tyr Pro Val Glu His Pro Val Glu Ile Ser Pro Gly Asp Ile Ile Ala
        235                 240                 245 acc agg tgt ctg ttc act ggt aaa ggc agg acg tca gca aca tat att       879
Thr Arg Cys Leu Phe Thr Gly Lys Gly Arg Thr Ser Ala Thr Tyr Ile
250                 255                 260                 265 ggt ggc aca tct aac gat gaa atg tgt aat tta tac atc atg tat tac       927
Gly Gly Thr Ser Asn Asp Glu Met Cys Asn Leu Tyr Ile Met Tyr Tyr
                270                 275                 280 atg gat gcg gcc cat gct acg tca tac atg acc tgt gta cag acg ggt       975
Met Asp Ala Ala His Ala Thr Ser Tyr Met Thr Cys Val Gln Thr Gly
            285                 290                 295 gaa cca aag tta ttt caa aac atc cct gag att gca aat gtt ccc att      1023
Glu Pro Lys Leu Phe Gln Asn Ile Pro Glu Ile Ala Asn Val Pro Ile
        300                 305                 310 cct gta agc cct gac atg atg atg taa                                  1050
Pro Val Ser Pro Asp Met Met Met
        315                 320

<210> SEQ ID NO 27
<211> LENGTH: 321
<212> TYPE: PRT
<213> ORGANISM: Artificial Sequence
<220> FEATURE:
<223> OTHER INFORMATION: Description of Artificial Sequence: Synthetic
      AE-I[1-321]C40A,C85A polypeptide

<400> SEQUENCE: 27

Ser Leu Ser Asn Asp Cys Leu Gly Thr Thr Arg Pro Val Met Ser Pro
1               5                   10                  15

Gly Ser Ser Asp Tyr Thr Leu Asp Ile Arg Met Pro Gly Val Thr Pro
            20                  25                  30

Thr Glu Ser Asp Thr Tyr Leu Ala Lys Ser Tyr Arg Leu Pro Val Asp
        35                  40                  45

Asp Glu Ala Tyr Val Val Asp Phe Arg Pro His Ala Asn Met Asp Thr
    50                  55                  60

Ala His His Met Leu Leu Phe Gly Cys Asn Ile Pro Ser Ser Thr Asp
65                  70                  75                  80

Asp Tyr Trp Asp Ala Ser Ala Gly Thr Cys Met Asp Lys Ser Ser Ile
                85                  90                  95

Met Tyr Ala Trp Ala Lys Asn Ala Pro Pro Thr Lys Leu Pro Glu Gly
            100                 105                 110

Val Gly Phe Arg Val Gly Gly Lys Ser Gly Ser Arg Tyr Phe Val Leu
        115                 120                 125

Gln Val His Tyr Gly Asn Val Lys Ala Phe Gln Asp Lys His Lys Asp
    130                 135                 140

Cys Thr Gly Val Thr Val Arg Val Thr Pro Glu Lys Gln Pro Gln Ile
145                 150                 155                 160

Ala Gly Ile Tyr Leu Ser Met Ser Val Asp Thr Val Ile Pro Pro Gly
                165                 170                 175

Glu Glu Ala Val Asn Ser Asp Ile Ala Cys Leu Tyr Asn Arg Pro Thr
            180                 185                 190

Ile His Pro Phe Ala Tyr Arg Val His Thr His Gln Leu Gly Gln Val
        195                 200                 205

Val Ser Gly Phe Arg Val Arg His Gly Lys Trp Ser Leu Ile Gly Arg
    210                 215                 220

Gln Ser Pro Gln Leu Pro Gln Ala Phe Tyr Pro Val Glu His Pro Val
```

```
                225                 230                 235                 240
Glu Ile Ser Pro Gly Asp Ile Ile Ala Thr Arg Cys Leu Phe Thr Gly
                    245                 250                 255
Lys Gly Arg Thr Ser Ala Thr Tyr Ile Gly Gly Thr Ser Asn Asp Glu
                260                 265                 270
Met Cys Asn Leu Tyr Ile Met Tyr Met Asp Ala Ala His Ala Thr
            275                 280                 285
Ser Tyr Met Thr Cys Val Gln Thr Gly Glu Pro Lys Leu Phe Gln Asn
                290                 295                 300
Ile Pro Glu Ile Ala Asn Val Pro Ile Pro Val Ser Pro Asp Met Met
305                 310                 315                 320
Met

<210> SEQ ID NO 28
<211> LENGTH: 1050
<212> TYPE: DNA
<213> ORGANISM: Artificial Sequence
<220> FEATURE:
<223> OTHER INFORMATION: Description of Artificial Sequence: Synthetic
      AE-I[1-321]C73A,C90A polynucleotide
<220> FEATURE:
<221> NAME/KEY: CDS
<222> LOCATION: (85)..(1047)

<400> SEQUENCE: 28
atgtcgtact accatcacca tcaccatcac gattacgata tcccaacgac cgaaaacctg     60
tattttcagg gcgccatgga tccg tca ctt tcc aat gac tgc ttg gga acc      111
                         Ser Leu Ser Asn Asp Cys Leu Gly Thr
                           1               5 acg cgg ccc gtt atg tct cca ggc tca tca gat tat act cta gat atc    159
Thr Arg Pro Val Met Ser Pro Gly Ser Ser Asp Tyr Thr Leu Asp Ile
 10                  15                  20                  25 cgc atg cca gga gta act ccg aca gag tcg gac aca tat ttg tgc aag    207
Arg Met Pro Gly Val Thr Pro Thr Glu Ser Asp Thr Tyr Leu Cys Lys
                 30                  35                  40 tct tac cgg ctg cca gtg gat gat gaa gcc tat gta gtt gac ttc aga    255
Ser Tyr Arg Leu Pro Val Asp Asp Glu Ala Tyr Val Val Asp Phe Arg
             45                  50                  55 cca cat gcc aat atg gat act gca cat cac atg ctt cta ttt gga gcc    303
Pro His Ala Asn Met Asp Thr Ala His His Met Leu Leu Phe Gly Ala
         60                  65                  70 aat ata cct tct tcc act gat gat tac tgg gac tgt agt gcg gga act    351
Asn Ile Pro Ser Ser Thr Asp Asp Tyr Trp Asp Cys Ser Ala Gly Thr
     75                  80                  85 gcc atg gac aaa tcc agt ata atg tat gcc tgg gca aag aat gca cca    399
Ala Met Asp Lys Ser Ser Ile Met Tyr Ala Trp Ala Lys Asn Ala Pro
 90                  95                 100                 105 ccc acc aaa ctt cca gaa gga gtt ggc ttt cgt gtt gga ggg aaa tca    447
Pro Thr Lys Leu Pro Glu Gly Val Gly Phe Arg Val Gly Gly Lys Ser
                110                 115                 120 ggc agt aga tat ttt gtg ctt caa gtt cac tat gga aat gtg aaa gca    495
Gly Ser Arg Tyr Phe Val Leu Gln Val His Tyr Gly Asn Val Lys Ala
            125                 130                 135 ttc cag gat aaa cat aaa gat tgc acg ggg gtg aca gta cga gta aca    543
Phe Gln Asp Lys His Lys Asp Cys Thr Gly Val Thr Val Arg Val Thr
        140                 145                 150 cct gaa aaa caa ccg caa att gca ggc att tat ctt tca atg tct gtg    591
Pro Glu Lys Gln Pro Gln Ile Ala Gly Ile Tyr Leu Ser Met Ser Val
    155                 160                 165 gac act gtt att cca cct ggg gaa gag gca gtt aat tct gat atc gcc    639
Asp Thr Val Ile Pro Pro Gly Glu Glu Ala Val Asn Ser Asp Ile Ala
```

```
Asp Thr Val Ile Pro Pro Gly Glu Glu Ala Val Asn Ser Asp Ile Ala
170                 175                 180                 185 tgc ctc tac aac agg ccg aca ata cac cca ttt gcc tac aga gtc cac       687
Cys Leu Tyr Asn Arg Pro Thr Ile His Pro Phe Ala Tyr Arg Val His
                190                 195                 200 act cat cag ttg ggg cag gtc gta agt gga ttt aga gtg aga cat ggc       735
Thr His Gln Leu Gly Gln Val Val Ser Gly Phe Arg Val Arg His Gly
                    205                 210                 215 aag tgg tct tta att ggt aga caa agc cca cag ctg cca cag gca ttt       783
Lys Trp Ser Leu Ile Gly Arg Gln Ser Pro Gln Leu Pro Gln Ala Phe
                220                 225                 230 tac cct gta gag cat cca gta gag att agc cct ggg gat att ata gca       831
Tyr Pro Val Glu His Pro Val Glu Ile Ser Pro Gly Asp Ile Ile Ala
235                 240                 245 acc agg tgt ctg ttc act ggt aaa ggc agg acg tca gca aca tat att       879
Thr Arg Cys Leu Phe Thr Gly Lys Gly Arg Thr Ser Ala Thr Tyr Ile
250                 255                 260                 265 ggt ggc aca tct aac gat gaa atg tgt aat tta tac atc atg tat tac       927
Gly Gly Thr Ser Asn Asp Glu Met Cys Asn Leu Tyr Ile Met Tyr Tyr
                270                 275                 280 atg gat gcg gcc cat gct acg tca tac atg acc tgt gta cag acg ggt       975
Met Asp Ala Ala His Ala Thr Ser Tyr Met Thr Cys Val Gln Thr Gly
                285                 290                 295 gaa cca aag tta ttt caa aac atc cct gag att gca aat gtt ccc att      1023
Glu Pro Lys Leu Phe Gln Asn Ile Pro Glu Ile Ala Asn Val Pro Ile
                300                 305                 310 cct gta agc cct gac atg atg atg taa                                  1050
Pro Val Ser Pro Asp Met Met Met
315                 320

<210> SEQ ID NO 29
<211> LENGTH: 321
<212> TYPE: PRT
<213> ORGANISM: Artificial Sequence
<220> FEATURE:
<223> OTHER INFORMATION: Description of Artificial Sequence: Synthetic
      AE-I[1-321]C73A,C90A polypeptide

<400> SEQUENCE: 29

Ser Leu Ser Asn Asp Cys Leu Gly Thr Thr Arg Pro Val Met Ser Pro
1               5                   10                  15

Gly Ser Ser Asp Tyr Thr Leu Asp Ile Arg Met Pro Gly Val Thr Pro
                20                  25                  30

Thr Glu Ser Asp Thr Tyr Leu Cys Lys Ser Tyr Arg Leu Pro Val Asp
            35                  40                  45

Asp Glu Ala Tyr Val Val Asp Phe Arg Pro His Ala Asn Met Asp Thr
        50                  55                  60

Ala His His Met Leu Leu Phe Gly Ala Asn Ile Pro Ser Ser Thr Asp
65                  70                  75                  80

Asp Tyr Trp Asp Cys Ser Ala Gly Thr Ala Met Asp Lys Ser Ser Ile
                85                  90                  95

Met Tyr Ala Trp Ala Lys Asn Ala Pro Pro Thr Lys Leu Pro Glu Gly
                100                 105                 110

Val Gly Phe Arg Val Gly Gly Lys Ser Gly Ser Arg Tyr Phe Val Leu
            115                 120                 125

Gln Val His Tyr Gly Asn Val Lys Ala Phe Gln Asp Lys His Lys Asp
        130                 135                 140

Cys Thr Gly Val Thr Val Arg Val Thr Pro Glu Lys Gln Pro Gln Ile
145                 150                 155                 160
```

```
Ala Gly Ile Tyr Leu Ser Met Ser Val Asp Thr Val Ile Pro Pro Gly
            165                 170                 175

Glu Glu Ala Val Asn Ser Asp Ile Ala Cys Leu Tyr Asn Arg Pro Thr
        180                 185                 190

Ile His Pro Phe Ala Tyr Arg Val His Thr His Gln Leu Gly Gln Val
        195                 200                 205

Val Ser Gly Phe Arg Val Arg His Gly Lys Trp Ser Leu Ile Gly Arg
    210                 215                 220

Gln Ser Pro Gln Leu Pro Gln Ala Phe Tyr Pro Val Glu His Pro Val
225                 230                 235                 240

Glu Ile Ser Pro Gly Asp Ile Ile Ala Thr Arg Cys Leu Phe Thr Gly
                245                 250                 255

Lys Gly Arg Thr Ser Ala Thr Tyr Ile Gly Gly Thr Ser Asn Asp Glu
            260                 265                 270

Met Cys Asn Leu Tyr Ile Met Tyr Met Asp Ala Ala His Ala Thr
        275                 280                 285

Ser Tyr Met Thr Cys Val Gln Thr Gly Glu Pro Lys Leu Phe Gln Asn
    290                 295                 300

Ile Pro Glu Ile Ala Asn Val Pro Ile Pro Val Ser Pro Asp Met Met
305                 310                 315                 320

Met
```

<210> SEQ ID NO 30
<211> LENGTH: 1050
<212> TYPE: DNA
<213> ORGANISM: Artificial Sequence
<220> FEATURE:
<223> OTHER INFORMATION: Description of Artificial Sequence: Synthetic
      AE-I[1-321]C186A,C293A polynucleotide
<220> FEATURE:
<221> NAME/KEY: CDS
<222> LOCATION: (85)..(1047)

<400> SEQUENCE: 30

```
atgtcgtact accatcacca tcaccatcac gattacgata tcccaacgac cgaaaacctg      60
tattttcagg gcgccatgga tccg tca ctt tcc aat gac tgc ttg gga acc       111
                          Ser Leu Ser Asn Asp Cys Leu Gly Thr
                           1               5 acg cgg ccc gtt atg tct cca ggc tca tca gat tat acc cta gat atc     159
Thr Arg Pro Val Met Ser Pro Gly Ser Ser Asp Tyr Thr Leu Asp Ile
 10                  15                  20                  25 cgc atg cca gga gta act ccg aca gag tcg gac aca tat ttg tgc aag     207
Arg Met Pro Gly Val Thr Pro Thr Glu Ser Asp Thr Tyr Leu Cys Lys
                 30                  35                  40 tct tac cgg ctg cca gtg gat gat gaa gcc tat gta gtt gac ttc aga     255
Ser Tyr Arg Leu Pro Val Asp Asp Glu Ala Tyr Val Val Asp Phe Arg
             45                  50                  55 cca cat gcc aat atg gat act gca cat cac atg ctt cta ttt gga tgc     303
Pro His Ala Asn Met Asp Thr Ala His His Met Leu Leu Phe Gly Cys
         60                  65                  70 aat ata cct tct tcc act gat gat tac tgg gac tgt agt gcg gga act     351
Asn Ile Pro Ser Ser Thr Asp Asp Tyr Trp Asp Cys Ser Ala Gly Thr
 75                  80                  85 tgc atg gac aaa tcc agt ata atg tat gcc tgg gca aag aat gca cca     399
Cys Met Asp Lys Ser Ser Ile Met Tyr Ala Trp Ala Lys Asn Ala Pro
 90                  95                 100                 105 ccc acc aaa ctt cca gaa gga gtt ggc ttt cgt gtt gga ggg aaa tca     447
Pro Thr Lys Leu Pro Glu Gly Val Gly Phe Arg Val Gly Gly Lys Ser
                110                 115                 120
```

```
ggc agt aga tat ttt gtg ctt caa gtt cac tat gga aat gtg aaa gca      495
Gly Ser Arg Tyr Phe Val Leu Gln Val His Tyr Gly Asn Val Lys Ala
            125                 130                 135 ttc cag gat aaa cat aaa gat tgc acg ggg gtg aca gta cga gta aca      543
Phe Gln Asp Lys His Lys Asp Cys Thr Gly Val Thr Val Arg Val Thr
        140                 145                 150 cct gaa aaa caa ccg caa att gca ggc att tat ctt tca atg tct gtg      591
Pro Glu Lys Gln Pro Gln Ile Ala Gly Ile Tyr Leu Ser Met Ser Val
    155                 160                 165 gac act gtt att cca cct ggg gaa gag gca gtt aat tct gat atc gcc      639
Asp Thr Val Ile Pro Pro Gly Glu Glu Ala Val Asn Ser Asp Ile Ala
170                 175                 180                 185 gcc ctc tac aac agg ccg aca ata cac cca ttt gcc tac aga gtc cac      687
Ala Leu Tyr Asn Arg Pro Thr Ile His Pro Phe Ala Tyr Arg Val His
                190                 195                 200 act cat cag ttg ggg cag gtc gta agt gga ttt aga gtg aga cat ggc      735
Thr His Gln Leu Gly Gln Val Val Ser Gly Phe Arg Val Arg His Gly
            205                 210                 215 aag tgg tct tta att ggt aga caa agc cca cag ctg cca cag gca ttt      783
Lys Trp Ser Leu Ile Gly Arg Gln Ser Pro Gln Leu Pro Gln Ala Phe
        220                 225                 230 tac cct gta gag cat cca gta gag att agc cct ggg gat att ata gca      831
Tyr Pro Val Glu His Pro Val Glu Ile Ser Pro Gly Asp Ile Ile Ala
    235                 240                 245 acc agg tgt ctg ttc act ggt aaa ggc agg acg tca gca aca tat att      879
Thr Arg Cys Leu Phe Thr Gly Lys Gly Arg Thr Ser Ala Thr Tyr Ile
250                 255                 260                 265 ggt ggc aca tct aac gat gaa atg tgt aat tta tac atc atg tat tac      927
Gly Gly Thr Ser Asn Asp Glu Met Cys Asn Leu Tyr Ile Met Tyr Tyr
                270                 275                 280 atg gat gcg gcc cat gct acg tca tac atg acc gct gta cag acg ggt      975
Met Asp Ala Ala His Ala Thr Ser Tyr Met Thr Ala Val Gln Thr Gly
            285                 290                 295 gaa cca aag tta ttt caa aac atc cct gag att gca aat gtt ccc att     1023
Glu Pro Lys Leu Phe Gln Asn Ile Pro Glu Ile Ala Asn Val Pro Ile
        300                 305                 310 cct gta agc cct gac atg atg atg taa                                 1050
Pro Val Ser Pro Asp Met Met Met
    315                 320

<210> SEQ ID NO 31
<211> LENGTH: 321
<212> TYPE: PRT
<213> ORGANISM: Artificial Sequence
<220> FEATURE:
<223> OTHER INFORMATION: Description of Artificial Sequence: Synthetic
      AE-I[1-321]C186A,C293A polypeptide

<400> SEQUENCE: 31

Ser Leu Ser Asn Asp Cys Leu Gly Thr Thr Arg Pro Val Met Ser Pro
1               5                   10                  15

Gly Ser Ser Asp Tyr Thr Leu Asp Ile Arg Met Pro Gly Val Thr Pro
                20                  25                  30

Thr Glu Ser Asp Thr Tyr Leu Cys Lys Ser Tyr Arg Leu Pro Val Asp
            35                  40                  45

Asp Glu Ala Tyr Val Val Asp Phe Arg Pro His Ala Asn Met Asp Thr
        50                  55                  60

Ala His His Met Leu Leu Phe Gly Cys Asn Ile Pro Ser Ser Thr Asp
65                  70                  75                  80

Asp Tyr Trp Asp Cys Ser Ala Gly Thr Cys Met Asp Lys Ser Ser Ile
                85                  90                  95
```

```
Met Tyr Ala Trp Ala Lys Asn Ala Pro Pro Thr Lys Leu Pro Glu Gly
            100                 105                 110

Val Gly Phe Arg Val Gly Gly Lys Ser Gly Ser Arg Tyr Phe Val Leu
        115                 120                 125

Gln Val His Tyr Gly Asn Val Lys Ala Phe Gln Asp Lys His Lys Asp
    130                 135                 140

Cys Thr Gly Val Thr Val Arg Val Thr Pro Glu Lys Gln Pro Gln Ile
145                 150                 155                 160

Ala Gly Ile Tyr Leu Ser Met Ser Val Asp Thr Val Ile Pro Pro Gly
                165                 170                 175

Glu Glu Ala Val Asn Ser Asp Ile Ala Ala Leu Tyr Asn Arg Pro Thr
            180                 185                 190

Ile His Pro Phe Ala Tyr Arg Val His Thr His Gln Leu Gly Gln Val
        195                 200                 205

Val Ser Gly Phe Arg Val Arg His Gly Lys Trp Ser Leu Ile Gly Arg
    210                 215                 220

Gln Ser Pro Gln Leu Pro Gln Ala Phe Tyr Pro Val Glu His Pro Val
225                 230                 235                 240

Glu Ile Ser Pro Gly Asp Ile Ile Ala Thr Arg Cys Leu Phe Thr Gly
                245                 250                 255

Lys Gly Arg Thr Ser Ala Thr Tyr Ile Gly Gly Thr Ser Asn Asp Glu
            260                 265                 270

Met Cys Asn Leu Tyr Ile Met Tyr Met Asp Ala Ala His Ala Thr
        275                 280                 285

Ser Tyr Met Thr Ala Val Gln Thr Gly Glu Pro Lys Leu Phe Gln Asn
    290                 295                 300

Ile Pro Glu Ile Ala Asn Val Pro Ile Pro Val Ser Pro Asp Met Met
305                 310                 315                 320

Met

<210> SEQ ID NO 32
<211> LENGTH: 1050
<212> TYPE: DNA
<213> ORGANISM: Artificial Sequence
<220> FEATURE:
<223> OTHER INFORMATION: Description of Artificial Sequence: Synthetic
      AE-I[1-321]C252A,C274A polynucleotide
<220> FEATURE:
<221> NAME/KEY: CDS
<222> LOCATION: (85)..(1047)

<400> SEQUENCE: 32
atgtcgtact accatcacca tcaccatcac gattacgata tcccaacgac cgaaaacctg      60
tattttcagg gcgccatgga tccg tca ctt tcc aat gac tgc ttg gga acc       111
                     Ser Leu Ser Asn Asp Cys Leu Gly Thr
                      1               5 acg cgg ccc gtt atg tct cca ggc tca tca gat tat act cta gat atc    159
Thr Arg Pro Val Met Ser Pro Gly Ser Ser Asp Tyr Thr Leu Asp Ile
 10              15                  20                  25 cgc atg cca gga gta act ccg aca gag tcg gac aca tat ttg tgc aag    207
Arg Met Pro Gly Val Thr Pro Thr Glu Ser Asp Thr Tyr Leu Cys Lys
             30                  35                  40 tct tac cgg ctg cca gtg gat gat gaa gcc tat gta gtt gac ttc aga    255
Ser Tyr Arg Leu Pro Val Asp Asp Glu Ala Tyr Val Val Asp Phe Arg
         45                  50                  55 cca cat gcc aat atg gat act gca cat cac atg ctt cta ttt gga tgc    303
Pro His Ala Asn Met Asp Thr Ala His His Met Leu Leu Phe Gly Cys
     60                  65                  70
```

```
aat ata cct tct tcc act gat gat tac tgg gac tgt agt gcg gga act      351
Asn Ile Pro Ser Ser Thr Asp Asp Tyr Trp Asp Cys Ser Ala Gly Thr
     75                  80                  85 tgc atg gac aaa tcc agt ata atg tat gcc tgg gca aag aat gca cca      399
Cys Met Asp Lys Ser Ser Ile Met Tyr Ala Trp Ala Lys Asn Ala Pro
 90                  95                 100                 105 ccc acc aaa ctt cca gaa gga gtt ggc ttt cgt gtt gga ggg aaa tca      447
Pro Thr Lys Leu Pro Glu Gly Val Gly Phe Arg Val Gly Gly Lys Ser
                110                 115                 120 ggc agt aga tat ttt gtg ctt caa gtt cac tat gga aat gtg aaa gca      495
Gly Ser Arg Tyr Phe Val Leu Gln Val His Tyr Gly Asn Val Lys Ala
            125                 130                 135 ttc cag gat aaa cat aaa gat tgc acg ggg gtg aca gta cga gta aca      543
Phe Gln Asp Lys His Lys Asp Cys Thr Gly Val Thr Val Arg Val Thr
        140                 145                 150 cct gaa aaa caa ccg caa att gca ggc att tat ctt tca atg tct gtg      591
Pro Glu Lys Gln Pro Gln Ile Ala Gly Ile Tyr Leu Ser Met Ser Val
    155                 160                 165 gac act gtt att cca cct ggg gaa gag gca gtt aat tct gat atc gcc      639
Asp Thr Val Ile Pro Pro Gly Glu Glu Ala Val Asn Ser Asp Ile Ala
170                 175                 180                 185 tgc ctc tac aac agg ccg aca ata cac cca ttt gcc tac aga gtc cac      687
Cys Leu Tyr Asn Arg Pro Thr Ile His Pro Phe Ala Tyr Arg Val His
                190                 195                 200 act cat cag ttg ggg cag gtc gta agt gga ttt aga gtg aga cat ggc      735
Thr His Gln Leu Gly Gln Val Val Ser Gly Phe Arg Val Arg His Gly
            205                 210                 215 aag tgg tct tta att ggt aga caa agc cca cag ctg cca cag gca ttt      783
Lys Trp Ser Leu Ile Gly Arg Gln Ser Pro Gln Leu Pro Gln Ala Phe
        220                 225                 230 tac cct gta gag cat cca gta gag att agc cct ggg gat att ata gca      831
Tyr Pro Val Glu His Pro Val Glu Ile Ser Pro Gly Asp Ile Ile Ala
    235                 240                 245 acc agg gct ctg ttc act ggt aaa ggc agg acg tca gca aca tat att      879
Thr Arg Ala Leu Phe Thr Gly Lys Gly Arg Thr Ser Ala Thr Tyr Ile
250                 255                 260                 265 ggt ggc aca tct aac gat gaa atg gct aat tta tac atc atg tat tac      927
Gly Gly Thr Ser Asn Asp Glu Met Ala Asn Leu Tyr Ile Met Tyr Tyr
                270                 275                 280 atg gat gcg gcc cat gct acg tca tac atg acc tgt gta cag acg ggt      975
Met Asp Ala Ala His Ala Thr Ser Tyr Met Thr Cys Val Gln Thr Gly
            285                 290                 295 gaa cca aag tta ttt caa aac atc cct gag att gca aat gtt ccc att     1023
Glu Pro Lys Leu Phe Gln Asn Ile Pro Glu Ile Ala Asn Val Pro Ile
        300                 305                 310 cct gta agc cct gac atg atg atg taa                                 1050
Pro Val Ser Pro Asp Met Met Met
    315                 320
```

<210> SEQ ID NO 33
<211> LENGTH: 321
<212> TYPE: PRT
<213> ORGANISM: Artificial Sequence
<220> FEATURE:
<223> OTHER INFORMATION: Description of Artificial Sequence: Synthetic
      AE-I[1-321]C252A,C274A polypeptide

<400> SEQUENCE: 33

```
Ser Leu Ser Asn Asp Cys Leu Gly Thr Thr Arg Pro Val Met Ser Pro
1               5                   10                  15

Gly Ser Ser Asp Tyr Thr Leu Asp Ile Arg Met Pro Gly Val Thr Pro
```

```
                    20                  25                  30
        Thr Glu Ser Asp Thr Tyr Leu Cys Lys Ser Tyr Arg Leu Pro Val Asp
                     35                  40                  45

Asp Glu Ala Tyr Val Val Asp Phe Arg Pro His Ala Asn Met Asp Thr
                     50                  55                  60

Ala His His Met Leu Leu Phe Gly Cys Asn Ile Pro Ser Ser Thr Asp
        65                  70                  75                  80

Asp Tyr Trp Asp Cys Ser Ala Gly Thr Cys Met Asp Lys Ser Ser Ile
                         85                  90                  95

Met Tyr Ala Trp Ala Lys Asn Ala Pro Pro Thr Lys Leu Pro Glu Gly
                    100                 105                 110

Val Gly Phe Arg Val Gly Gly Lys Ser Gly Ser Arg Tyr Phe Val Leu
                    115                 120                 125

Gln Val His Tyr Gly Asn Val Lys Ala Phe Gln Asp Lys His Lys Asp
                    130                 135                 140

Cys Thr Gly Val Thr Val Arg Val Thr Pro Glu Lys Gln Pro Gln Ile
        145                 150                 155                 160

Ala Gly Ile Tyr Leu Ser Met Ser Val Asp Thr Val Ile Pro Pro Gly
                        165                 170                 175

Glu Glu Ala Val Asn Ser Asp Ile Ala Cys Leu Tyr Asn Arg Pro Thr
                    180                 185                 190

Ile His Pro Phe Ala Tyr Arg Val His Thr His Gln Leu Gly Gln Val
                    195                 200                 205

Val Ser Gly Phe Arg Val Arg His Gly Lys Trp Ser Leu Ile Gly Arg
                    210                 215                 220

Gln Ser Pro Gln Leu Pro Gln Ala Phe Tyr Pro Val Glu His Pro Val
        225                 230                 235                 240

Glu Ile Ser Pro Gly Asp Ile Ile Ala Thr Arg Ala Leu Phe Thr Gly
                        245                 250                 255

Lys Gly Arg Thr Ser Ala Thr Tyr Ile Gly Gly Thr Ser Asn Asp Glu
                    260                 265                 270

Met Ala Asn Leu Tyr Ile Met Tyr Tyr Met Asp Ala Ala His Ala Thr
                    275                 280                 285

Ser Tyr Met Thr Cys Val Gln Thr Gly Glu Pro Lys Leu Phe Gln Asn
                    290                 295                 300

Ile Pro Glu Ile Ala Asn Val Pro Ile Pro Val Ser Pro Asp Met Met
        305                 310                 315                 320

Met

<210> SEQ ID NO 34
<211> LENGTH: 1029
<212> TYPE: DNA
<213> ORGANISM: Artificial Sequence
<220> FEATURE:
<223> OTHER INFORMATION: Description of Artificial Sequence: Synthetic
      AE-I[8-321]C145A,C40A,C85A polynucleotide
<220> FEATURE:
<221> NAME/KEY: CDS
<222> LOCATION: (85)..(1026)

<400> SEQUENCE: 34
atgtcgtact accatcacca tcaccatcac gattacgata tcccaacgac cgaaaacctg       60
tattttcagg gcgccatgga tccg gga acc acg cgg ccc gtt atg tct cca         111
                          Gly Thr Thr Arg Pro Val Met Ser Pro
                            1               5 ggc tca tca gat tat act cta gat atc cgc atg cca gga gta act ccg        159
Gly Ser Ser Asp Tyr Thr Leu Asp Ile Arg Met Pro Gly Val Thr Pro
```

```
              10                  15                  20                  25
aca gag tcg gac aca tat ttg gcc aag tct tac cgg ctg cca gtg gat          207
Thr Glu Ser Asp Thr Tyr Leu Ala Lys Ser Tyr Arg Leu Pro Val Asp
                         30                  35                  40 gat gaa gcc tat gta gtt gac ttc aga cca cat gcc aat atg gat act          255
Asp Glu Ala Tyr Val Val Asp Phe Arg Pro His Ala Asn Met Asp Thr
                 45                  50                  55 gca cat cac atg ctt cta ttt gga tgc aat ata cct tct tcc act gat          303
Ala His His Met Leu Leu Phe Gly Cys Asn Ile Pro Ser Ser Thr Asp
             60                  65                  70 gat tac tgg gac gct agt gcg gga act tgc atg gac aaa tcc agt ata          351
Asp Tyr Trp Asp Ala Ser Ala Gly Thr Cys Met Asp Lys Ser Ser Ile
         75                  80                  85 atg tat gcc tgg gca aag aat gca cca ccc acc aaa ctt cca gaa gga          399
Met Tyr Ala Trp Ala Lys Asn Ala Pro Pro Thr Lys Leu Pro Glu Gly
 90                  95                 100                 105 gtt ggc ttt cgt gtt gga ggg aaa tca ggc agt aga tat ttt gtg ctt          447
Val Gly Phe Arg Val Gly Gly Lys Ser Gly Ser Arg Tyr Phe Val Leu
                    110                 115                 120 caa gtt cac tat gga aat gtg aaa gca ttc cag gat aaa cat aaa gat          495
Gln Val His Tyr Gly Asn Val Lys Ala Phe Gln Asp Lys His Lys Asp
                125                 130                 135 gcc acg ggg gtg aca gta cga gta aca cct gaa aaa caa ccg caa att          543
Ala Thr Gly Val Thr Val Arg Val Thr Pro Glu Lys Gln Pro Gln Ile
            140                 145                 150 gca ggc att tat ctt tca atg tct gtg gac act gtt att cca cct ggg          591
Ala Gly Ile Tyr Leu Ser Met Ser Val Asp Thr Val Ile Pro Pro Gly
        155                 160                 165 gaa gag gca gtt aat tct gat atc gcc tgc ctc tac aac agg ccg aca          639
Glu Glu Ala Val Asn Ser Asp Ile Ala Cys Leu Tyr Asn Arg Pro Thr
170                 175                 180                 185 ata cac cca ttt gcc tac aga gtc cac act cat cag ttg ggg cag gtc          687
Ile His Pro Phe Ala Tyr Arg Val His Thr His Gln Leu Gly Gln Val
                    190                 195                 200 gta agt gga ttt aga gtg aga cat ggc aag tgg tct tta att ggt aga          735
Val Ser Gly Phe Arg Val Arg His Gly Lys Trp Ser Leu Ile Gly Arg
                205                 210                 215 caa agc cca cag ctg cca cag gca ttt tac cct gta gag cat cca gta          783
Gln Ser Pro Gln Leu Pro Gln Ala Phe Tyr Pro Val Glu His Pro Val
            220                 225                 230 gag att agc cct ggg gat att ata gca acc agg tgt ctg ttc act ggt          831
Glu Ile Ser Pro Gly Asp Ile Ile Ala Thr Arg Cys Leu Phe Thr Gly
        235                 240                 245 aaa ggc agg acg tca gca aca tat att ggt ggc aca tct aac gat gaa          879
Lys Gly Arg Thr Ser Ala Thr Tyr Ile Gly Gly Thr Ser Asn Asp Glu
250                 255                 260                 265 atg tgt aat tta tac atc atg tat tac atg gat gcg gcc cat gct acg          927
Met Cys Asn Leu Tyr Ile Met Tyr Tyr Met Asp Ala Ala His Ala Thr
                    270                 275                 280 tca tac atg acc tgt gta cag acg ggt gaa cca aag tta ttt caa aac          975
Ser Tyr Met Thr Cys Val Gln Thr Gly Glu Pro Lys Leu Phe Gln Asn
                285                 290                 295 atc cct gag att gca aat gtt ccc att cct gta agc cct gac atg atg         1023
Ile Pro Glu Ile Ala Asn Val Pro Ile Pro Val Ser Pro Asp Met Met
            300                 305                 310 atg taa                                                                 1029
Met

<210> SEQ ID NO 35
<211> LENGTH: 314
```

```
<212> TYPE: PRT
<213> ORGANISM: Artificial Sequence
<220> FEATURE:
<223> OTHER INFORMATION: Description of Artificial Sequence: Synthetic
      AE-I[8-321]C145A,C40A,C85A polypeptide

<400> SEQUENCE: 35

Gly Thr Thr Arg Pro Val Met Ser Pro Gly Ser Ser Asp Tyr Thr Leu
1               5                   10                  15

Asp Ile Arg Met Pro Gly Val Thr Pro Thr Glu Ser Thr Tyr Leu
            20                  25                  30

Ala Lys Ser Tyr Arg Leu Pro Val Asp Asp Glu Ala Tyr Val Val Asp
        35                  40                  45

Phe Arg Pro His Ala Asn Met Asp Thr Ala His His Met Leu Leu Phe
    50                  55                  60

Gly Cys Asn Ile Pro Ser Ser Thr Asp Tyr Trp Asp Ala Ser Ala
65                  70                  75                  80

Gly Thr Cys Met Asp Lys Ser Ser Ile Met Tyr Ala Trp Ala Lys Asn
                85                  90                  95

Ala Pro Pro Thr Lys Leu Pro Glu Gly Val Gly Phe Arg Val Gly Gly
            100                 105                 110

Lys Ser Gly Ser Arg Tyr Phe Val Leu Gln Val His Tyr Gly Asn Val
        115                 120                 125

Lys Ala Phe Gln Asp Lys His Lys Asp Ala Thr Gly Val Thr Val Arg
    130                 135                 140

Val Thr Pro Glu Lys Gln Pro Gln Ile Ala Gly Ile Tyr Leu Ser Met
145                 150                 155                 160

Ser Val Asp Thr Val Ile Pro Pro Gly Glu Glu Ala Val Asn Ser Asp
                165                 170                 175

Ile Ala Cys Leu Tyr Asn Arg Pro Thr Ile His Pro Phe Ala Tyr Arg
            180                 185                 190

Val His Thr His Gln Leu Gly Gln Val Val Ser Gly Phe Arg Val Arg
        195                 200                 205

His Gly Lys Trp Ser Leu Ile Gly Arg Gln Ser Pro Gln Leu Pro Gln
    210                 215                 220

Ala Phe Tyr Pro Val Glu His Pro Val Glu Ile Ser Pro Gly Asp Ile
225                 230                 235                 240

Ile Ala Thr Arg Cys Leu Phe Thr Gly Lys Gly Arg Thr Ser Ala Thr
                245                 250                 255

Tyr Ile Gly Gly Thr Ser Asn Asp Glu Met Cys Asn Leu Tyr Ile Met
            260                 265                 270

Tyr Tyr Met Asp Ala Ala His Ala Thr Ser Tyr Met Thr Cys Val Gln
        275                 280                 285

Thr Gly Glu Pro Lys Leu Phe Gln Asn Ile Pro Glu Ile Ala Asn Val
    290                 295                 300

Pro Ile Pro Val Ser Pro Asp Met Met Met
305                 310

<210> SEQ ID NO 36
<211> LENGTH: 1050
<212> TYPE: DNA
<213> ORGANISM: Artificial Sequence
<220> FEATURE:
<223> OTHER INFORMATION: Description of Artificial Sequence: Synthetic
      AE-I[1-321]C40A,C85A,C252A,C274A polynucleotide
<220> FEATURE:
<221> NAME/KEY: CDS
<222> LOCATION: (85)..(1047)
```

<400> SEQUENCE: 36

```
atgtcgtact accatcacca tcaccatcac gattacgata tcccaacgac cgaaaacctg     60
tattttcagg gcgccatgga tccg tca ctt tcc aat gac tgc ttg gga acc       111
                          Ser Leu Ser Asn Asp Cys Leu Gly Thr
                          1               5 acg cgg ccc gtt atg tct cca ggc tca tca gat tat act cta gat atc      159
Thr Arg Pro Val Met Ser Pro Gly Ser Ser Asp Tyr Thr Leu Asp Ile
10              15                  20                  25 cgc atg cca gga gta act ccg aca gag tcg gac aca tat ttg gcc aag      207
Arg Met Pro Gly Val Thr Pro Thr Glu Ser Asp Thr Tyr Leu Ala Lys
                30                  35                  40 tct tac cgg ctg cca gtg gat gat gaa gcc tat gta gtt gac ttc aga      255
Ser Tyr Arg Leu Pro Val Asp Asp Glu Ala Tyr Val Val Asp Phe Arg
            45                  50                  55 cca cat gcc aat atg gat act gca cat cac atg ctt cta ttt gga tgc      303
Pro His Ala Asn Met Asp Thr Ala His His Met Leu Leu Phe Gly Cys
                60                  65                  70 aat ata cct tct tcc act gat gat tac tgg gac gct agt gcg gga act      351
Asn Ile Pro Ser Ser Thr Asp Asp Tyr Trp Asp Ala Ser Ala Gly Thr
75                  80                  85 tgc atg gac aaa tcc agt ata atg tat gcc tgg gca aag aat gca cca      399
Cys Met Asp Lys Ser Ser Ile Met Tyr Ala Trp Ala Lys Asn Ala Pro
90                  95                  100                 105 ccc acc aaa ctt cca gaa gga gtt ggc ttt cgt gtt gga ggg aaa tca      447
Pro Thr Lys Leu Pro Glu Gly Val Gly Phe Arg Val Gly Gly Lys Ser
                110                 115                 120 ggc agt aga tat ttt gtg ctt caa gtt cac tat gga aat gtg aaa gca      495
Gly Ser Arg Tyr Phe Val Leu Gln Val His Tyr Gly Asn Val Lys Ala
            125                 130                 135 ttc cag gat aaa cat aaa gat tgc acg ggg gtg aca gta cga gta aca      543
Phe Gln Asp Lys His Lys Asp Cys Thr Gly Val Thr Val Arg Val Thr
        140                 145                 150 cct gaa aaa caa ccg caa att gca ggg att tat ctt tca atg tct gtg      591
Pro Glu Lys Gln Pro Gln Ile Ala Gly Ile Tyr Leu Ser Met Ser Val
155                 160                 165 gac act gtt att cca cct ggg gaa gag gca gtt aat tct gat atc gcc      639
Asp Thr Val Ile Pro Pro Gly Glu Glu Ala Val Asn Ser Asp Ile Ala
170                 175                 180                 185 tgc ctc tac aac agg ccg aca ata cac cca ttt gcc tac aga gtc cac      687
Cys Leu Tyr Asn Arg Pro Thr Ile His Pro Phe Ala Tyr Arg Val His
                190                 195                 200 act cat cag ttg ggg cag gtc gta agt gga ttt aga gtg aga cat ggc      735
Thr His Gln Leu Gly Gln Val Val Ser Gly Phe Arg Val Arg His Gly
            205                 210                 215 aag tgg tct tta att ggt aga caa agc cca cag ctg cca cag gca ttt      783
Lys Trp Ser Leu Ile Gly Arg Gln Ser Pro Gln Leu Pro Gln Ala Phe
        220                 225                 230 tac cct gta gag cat cca gta gag att agc cct ggg gat att ata gca      831
Tyr Pro Val Glu His Pro Val Glu Ile Ser Pro Gly Asp Ile Ile Ala
235                 240                 245 acc agg gct ctg ttc act ggt aaa ggc agg acg tca gca aca tat att      879
Thr Arg Ala Leu Phe Thr Gly Lys Gly Arg Thr Ser Ala Thr Tyr Ile
250                 255                 260                 265 ggt ggc aca tct aac gat gaa atg gct aat tta tac atc atg tat tac      927
Gly Gly Thr Ser Asn Asp Glu Met Ala Asn Leu Tyr Ile Met Tyr Tyr
                270                 275                 280 atg gat gcg gcc cat gct acg tca tac atg acc tgt gta cag acg ggt      975
Met Asp Ala Ala His Ala Thr Ser Tyr Met Thr Cys Val Gln Thr Gly
            285                 290                 295
```

```
gaa cca aag tta ttt caa aac atc cct gag att gca aat gtt ccc att    1023
Glu Pro Lys Leu Phe Gln Asn Ile Pro Glu Ile Ala Asn Val Pro Ile
        300                 305                 310 cct gta agc cct gac atg atg atg taa                                1050
Pro Val Ser Pro Asp Met Met Met
    315                 320
```

<210> SEQ ID NO 37
<211> LENGTH: 321
<212> TYPE: PRT
<213> ORGANISM: Artificial Sequence
<220> FEATURE:
<223> OTHER INFORMATION: Description of Artificial Sequence: Synthetic
      AE-I[1-321]C40A,C85A,C252A,C274A polypeptide

<400> SEQUENCE: 37

```
Ser Leu Ser Asn Asp Cys Leu Gly Thr Thr Arg Pro Val Met Ser Pro
1               5                   10                  15

Gly Ser Ser Asp Tyr Thr Leu Asp Ile Arg Met Pro Gly Val Thr Pro
            20                  25                  30

Thr Glu Ser Asp Thr Tyr Leu Ala Lys Ser Tyr Arg Leu Pro Val Asp
        35                  40                  45

Asp Glu Ala Tyr Val Val Asp Phe Arg Pro His Ala Asn Met Asp Thr
    50                  55                  60

Ala His His Met Leu Leu Phe Gly Cys Asn Ile Pro Ser Ser Thr Asp
65                  70                  75                  80

Asp Tyr Trp Asp Ala Ser Ala Gly Thr Cys Met Asp Lys Ser Ser Ile
                85                  90                  95

Met Tyr Ala Trp Ala Lys Asn Ala Pro Pro Thr Lys Leu Pro Glu Gly
            100                 105                 110

Val Gly Phe Arg Val Gly Gly Lys Ser Gly Ser Arg Tyr Phe Val Leu
        115                 120                 125

Gln Val His Tyr Gly Asn Val Lys Ala Phe Gln Asp Lys His Lys Asp
    130                 135                 140

Cys Thr Gly Val Thr Val Arg Val Thr Pro Glu Lys Gln Pro Gln Ile
145                 150                 155                 160

Ala Gly Ile Tyr Leu Ser Met Ser Val Asp Thr Val Ile Pro Pro Gly
                165                 170                 175

Glu Glu Ala Val Asn Ser Asp Ile Ala Cys Leu Tyr Asn Arg Pro Thr
            180                 185                 190

Ile His Pro Phe Ala Tyr Arg Val His Thr His Gln Leu Gly Gln Val
        195                 200                 205

Val Ser Gly Phe Arg Val Arg His Gly Lys Trp Ser Leu Ile Gly Arg
    210                 215                 220

Gln Ser Pro Gln Leu Pro Gln Ala Phe Tyr Pro Val Glu His Pro Val
225                 230                 235                 240

Glu Ile Ser Pro Gly Asp Ile Ile Ala Thr Arg Ala Leu Phe Thr Gly
                245                 250                 255

Lys Gly Arg Thr Ser Ala Thr Tyr Ile Gly Gly Thr Ser Asn Asp Glu
            260                 265                 270

Met Ala Asn Leu Tyr Ile Met Tyr Tyr Met Asp Ala Ala His Ala Thr
        275                 280                 285

Ser Tyr Met Thr Cys Val Gln Thr Gly Glu Pro Lys Leu Phe Gln Asn
    290                 295                 300

Ile Pro Glu Ile Ala Asn Val Pro Ile Pro Val Ser Pro Asp Met Met
305                 310                 315                 320

Met
```

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 38

```
His His His His His His
1               5
```

<210> SEQ ID NO 39
<211> LENGTH: 400
<212> TYPE: PRT
<213> ORGANISM: Xenopus leavis

<400> SEQUENCE: 39

```
Met Ala Ser Leu Ser Ser Phe Leu Val Leu Phe Leu Leu Phe Gln
1               5                   10                  15

Asn Ser Cys Tyr Cys Phe Arg Ser Pro Leu Ser Val Phe Lys Arg Tyr
            20                  25                  30

Glu Glu Ser Thr Arg Ser Leu Ser Asn Asp Cys Leu Gly Thr Thr Arg
        35                  40                  45

Pro Val Met Ser Pro Gly Ser Ser Asp Tyr Thr Leu Asp Ile Arg Met
    50                  55                  60

Pro Gly Val Thr Pro Thr Glu Ser Asp Thr Tyr Leu Cys Lys Ser Tyr
65                  70                  75                  80

Arg Leu Pro Val Asp Asp Glu Ala Tyr Val Val Asp Phe Arg Pro His
                85                  90                  95

Ala Asn Met Asp Thr Ala His His Met Leu Leu Phe Gly Cys Asn Ile
            100                 105                 110

Pro Ser Ser Thr Asp Asp Tyr Trp Asp Cys Ser Ala Gly Thr Cys Met
        115                 120                 125

Asp Lys Ser Ser Ile Met Tyr Ala Trp Ala Lys Asn Ala Pro Pro Thr
    130                 135                 140

Lys Leu Pro Glu Gly Val Gly Phe Arg Val Gly Gly Lys Ser Gly Ser
145                 150                 155                 160

Arg Tyr Phe Val Leu Gln Val His Tyr Gly Asn Val Lys Ala Phe Gln
                165                 170                 175

Asp Lys His Lys Asp Cys Thr Gly Val Thr Val Arg Val Thr Pro Glu
            180                 185                 190

Lys Gln Pro Gln Ile Ala Gly Ile Tyr Leu Ser Met Ser Val Asp Thr
        195                 200                 205

Val Ile Pro Pro Gly Glu Glu Ala Val Asn Ser Asp Ile Ala Cys Leu
    210                 215                 220

Tyr Asn Arg Pro Thr Ile His Pro Phe Ala Tyr Arg Val His Thr His
225                 230                 235                 240

Gln Leu Gly Gln Val Val Ser Gly Phe Arg Val Arg His Gly Lys Trp
                245                 250                 255

Ser Leu Ile Gly Arg Gln Ser Pro Gln Leu Pro Gln Ala Phe Tyr Pro
            260                 265                 270

Val Glu His Pro Val Glu Ile Ser Pro Gly Asp Ile Ala Thr Arg
        275                 280                 285

Cys Leu Phe Thr Gly Lys Gly Arg Thr Ser Ala Thr Tyr Ile Gly Gly
    290                 295                 300
```

```
Thr Ser Asn Asp Glu Met Cys Asn Leu Tyr Ile Met Tyr Met Asp
305                 310                 315                 320

Ala Ala His Ala Thr Ser Tyr Met Thr Cys Val Gln Thr Gly Glu Pro
                325                 330                 335

Lys Leu Phe Gln Asn Ile Pro Glu Ile Ala Asn Val Pro Ile Pro Val
                340                 345                 350

Ser Pro Asp Met Met Met Met Gly His Gly His His Thr Glu
                355                 360                 365

Ala Glu Pro Glu Lys Asn Thr Gly Leu Gln Gln Pro Lys Arg Glu Glu
370                 375                 380

Glu Glu Val Leu Asp Gln Gly Leu Ile Thr Leu Gly Asp Ser Ala Val
385                 390                 395                 400

<210> SEQ ID NO 40
<211> LENGTH: 400
<212> TYPE: PRT
<213> ORGANISM: Rattus sp.

<400> SEQUENCE: 40

Met Ala Gly Arg Ala Arg Ser Gly Leu Leu Leu Leu Leu Gly Leu
1               5                   10                  15

Leu Ala Leu Gln Ser Ser Cys Leu Ala Phe Arg Ser Pro Leu Ser Val
                20                  25                  30

Phe Lys Arg Phe Lys Glu Thr Thr Arg Ser Phe Ser Asn Glu Cys Leu
                35                  40                  45

Gly Thr Ile Gly Pro Val Thr Pro Leu Asp Ala Ser Asp Phe Ala Leu
        50                  55                  60

Asp Ile Arg Met Pro Gly Val Thr Pro Lys Glu Ser Asp Thr Tyr Phe
65                  70                  75                  80

Cys Met Ser Met Arg Leu Pro Val Asp Glu Glu Ala Phe Val Ile Asp
                85                  90                  95

Phe Lys Pro Arg Ala Ser Met Asp Thr Val His His Met Leu Leu Phe
                100                 105                 110

Gly Cys Asn Met Pro Ser Ser Thr Gly Ser Tyr Trp Phe Cys Asp Glu
                115                 120                 125

Gly Thr Cys Thr Asp Lys Ala Asn Ile Leu Tyr Ala Trp Ala Arg Asn
        130                 135                 140

Ala Pro Pro Thr Arg Leu Pro Lys Gly Val Gly Phe Arg Val Gly Gly
145                 150                 155                 160

Glu Thr Gly Ser Lys Tyr Phe Val Leu Gln Val His Tyr Gly Asp Ile
                165                 170                 175

Ser Ala Phe Arg Asp Asn His Lys Asp Cys Ser Gly Val Ser Val His
                180                 185                 190

Leu Thr Arg Val Pro Gln Pro Leu Ile Ala Gly Met Tyr Leu Met Met
        195                 200                 205

Ser Val Asp Thr Val Ile Pro Pro Gly Glu Lys Val Val Asn Ala Asp
210                 215                 220

Ile Ser Cys Gln Tyr Lys Met Tyr Pro Met His Val Phe Ala Tyr Arg
225                 230                 235                 240

Val His Thr His His Leu Gly Lys Val Val Ser Gly Tyr Arg Val Arg
                245                 250                 255

Asn Gly Gln Trp Thr Leu Ile Gly Arg Gln Asn Pro Gln Leu Pro Gln
                260                 265                 270

Ala Phe Tyr Pro Val Glu His Pro Val Asp Val Thr Phe Gly Asp Ile
        275                 280                 285
```

```
Leu Ala Ala Arg Cys Val Phe Thr Gly Glu Gly Arg Thr Glu Ala Thr
    290             295             300
His Ile Gly Gly Thr Ser Ser Asp Glu Met Cys Asn Leu Tyr Ile Met
305             310             315                     320
Tyr Tyr Met Glu Ala Lys Tyr Ala Leu Ser Phe Met Thr Cys Thr Lys
            325             330                 335
Asn Val Ala Pro Asp Met Phe Arg Thr Ile Pro Ala Glu Ala Asn Ile
            340             345             350
Pro Ile Pro Val Lys Pro Asp Met Val Met Met His Gly His His Lys
        355             360             365
Glu Ala Glu Asn Lys Glu Lys Ser Ala Leu Met Gln Gln Pro Lys Gln
    370             375             380
Gly Glu Glu Glu Val Leu Glu Gln Gly Asp Phe Tyr Ser Leu Leu Ser
385             390             395             400
```